United States Patent [19]

Farr

[11] Patent Number: 5,589,337

[45] Date of Patent: *Dec. 31, 1996

[54] METHODS AND DIAGNOSTIC KITS FOR DETERMINING TOXICITY UTILIZING BACTERIAL STRESS PROMOTERS FUSED TO REPORTER GENES

[75] Inventor: Spencer B. Farr, Longmont, Colo.

[73] Assignee: The President and Fellows of Harvard College, Cambridge, Mass.

[*] Notice: The term of this patent shall not extend beyond the expiration date of Pat. No. 5,585,232.

[21] Appl. No.: 367,122

[22] PCT Filed: Jul. 6, 1993

[86] PCT No.: PCT/US93/06537

§ 371 Date: Jan. 6, 1995

§ 102(e) Date: Jan. 6, 1995

[87] PCT Pub. No.: WO94/01584

PCT Pub. Date: Jan. 20, 1994

Related U.S. Application Data

[63] Continuation-in-part of Ser. No. 910,793, Jul. 6, 1992, abandoned.

[51] Int. Cl.$^6$ .............................. C12Q 1/68; C12Q 1/02; C12N 15/63

[52] U.S. Cl. ................... 435/6; 435/29; 935/33; 935/38; 935/41; 935/43

[58] Field of Search ........................... 435/6, 29, 4, 69.1; 935/33, 38, 41, 43

[56] References Cited

U.S. PATENT DOCUMENTS

| | | | |
|---|---|---|---|
| 4,569,916 | 2/1986 | Penman et al. | 436/64 |
| 4,849,335 | 7/1989 | Hofnung et al. | 435/6 |
| 5,364,780 | 11/1994 | Hershey et al. | 435/172.3 |

FOREIGN PATENT DOCUMENTS

| | | |
|---|---|---|
| 0063522 | 10/1982 | European Pat. Off. . |
| 0370813 | 5/1990 | European Pat. Off. . |

OTHER PUBLICATIONS

Minagawa et al J. Biol. Chem. 265(19) 1990 11198–11203.
Farr et al Microbiol. Rev. 55(4) 1991 561–585.
Demple et al BioEssays 6(4) 1987 157–160.
Touati J. Bacteriol 2511–2520 1988 170(6).
Keyse et al PNAS 86 99–103 1989.
McCann et al PNAS 72(12) 5135–5139 1975.
Cowing et al PNAS 82 2679–2683 1985.
Ross et al J Bacteriol 171(7)4009–4018 1989.
Kuwajima et al J Bacteriol 168(3) 1986 1479–1483.
Neidhardt et al E. coli & S. typhimurium pp. 170–200 1987.
Lilley et al. Mol. Microbiol 5(4) 779–783 1991.
Kanazawa et al Biochem Biophys Res. Comm 604–612 103(2) 1981.

(List continued on next page.)

*Primary Examiner*—Mindy Fleisher
*Assistant Examiner*—Nancy J. Degen
*Attorney, Agent, or Firm*—Fish & Neave; James F. Haley, Jr.; Andrew S. Marks

[57] ABSTRACT

This invention provides methods and diagnostic kits for determining the toxicity of a compound. The methods and diagnostic kits of this invention employ a plurality of bacterial hosts, each of which harbors a DNA sequence encoding a different stress promoter fused to a gene which encodes an assayable product. Each of these stress promoters is induced by exposure to a different type of cellular stress. The stress promoters utilized in this invention, in toto, comprise those promoters which respond to redox stress, DNA stress, protein stress, energy stress and pH stress. The methods and diagnostic kits of this invention may be employed to characterize and quantify the toxicity of a compound, as well as to identify the cellular mechanism of its toxic action. Moreover, the methods of this invention yield information concerning the action of a compound on a subcellular level. This information may be utilized to design antitoxins to compounds found to be toxic and in active drug design.

23 Claims, 12 Drawing Sheets

OTHER PUBLICATIONS

Tse–Dinh et al J Mol Biol 202 735–742 1988.
Bruckman et al J Mol Biol 212 669–687 1990.
Kenyon et al J Mol Biol 160 445–457 1982.
Gushima et al Nuc. Acid Res. 12(24) 1984 9299–9307.
Drlica et al Biochemistry 27(7) 1988 2253–2259.
Triggs–Raine et al Gene 52 1987 121–128.
Javor et al 170(7) 1988 3291–3293 J. Bacteriol.
Saporito et al J Bacteriol. 170(11) 1988 5141–5145.
Loewen et al J Bacteriol 162(2) 1985 661–667.
Silverman et al J Bacteriol 120(3) 1974 1196–1203.
Kitagawa et al J Bacteriol 173(14) 1991 4247–4253.
Iuchi et al J Bacteriol 172(10) 6020–6025 1990.
Storz et al J Bacteriol 171(4) 1989 2049–2055.
von Mayenburg et al EMBOJ 4(9) 1985 2357–2363.
Chin et al J Biol Chem 263(24) 1988 11718–11728.
Hassan et al. PNAS 89 3217–3221 1992.
Kogoma et al PNAS 85 4799–4803 1988.
Ner et al Biochemistry 22(23) 5243–5249 1983.
Maki et al Nature 355 273–275 1992.

SEQUENCE LISTING ( 1 ) GENERAL INFORMATION:

( i i i ) NUMBER OF SEQUENCES: 54

( 2 ) INFORMATION FOR SEQ ID NO:1:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:1:

ACGAAAAGTA CGGCATTGAT                                                              20

( 2 ) INFORMATION FOR SEQ ID NO:2:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

GCTCATATTC ATCTCCAGTA                                                              20

( 2 ) INFORMATION FOR SEQ ID NO:3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

GCTATGTGTG TGATGTGAGC                                                              20

( 2 ) INFORMATION FOR SEQ ID NO:4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

TGATGACAGA TGTCGCCCCA                                                              20

( 2 ) INFORMATION FOR SEQ ID NO:5:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

CAGGTGCGTT GTAGTGAGTT                                                              20

( 2 ) INFORMATION FOR SEQ ID NO:6:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

CAATAAACGA GATAACTCTC C                                                            21

( 2 ) INFORMATION FOR SEQ ID NO:7:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

AAGCTTAATT AAGATCAATT TG                                                           22

( 2 ) INFORMATION FOR SEQ ID NO:8:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:8:

GCCGCAGAAA GCGGTTCGCC                                                                                      20

( 2 ) INFORMATION FOR SEQ ID NO:9:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:9:

ATCGGGTTGT TAGTTAACGC                                                                                      20

( 2 ) INFORMATION FOR SEQ ID NO:10:

( i ) SEQUENCE CHARACTERISTICS:
           ( A ) LENGTH: 22 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:10:

CTATACTTCC TCCGTGTTTT CG                                                                                22

( 2 ) INFORMATION FOR SEQ ID NO:11:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:11:

CATCGCATAA ACCACTACAT                                                                                     20

( 2 ) INFORMATION FOR SEQ ID NO:12:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:12:

GTTACTGCCC TGACCGGCGG                                                                                     20

( 2 ) INFORMATION FOR SEQ ID NO:13:

( i ) SEQUENCE CHARACTERISTICS:
           ( A ) LENGTH: 20 base pairs
           ( B ) TYPE: nucleic acid
           ( C ) STRANDEDNESS: single
           ( D ) TOPOLOGY: linear ( x i ) SEQUENCE DESCRIPTION: SEQ ID NO:13:

GAATTCGACC GCCATTGCGC                                                                                     20

( 2 ) INFORMATION FOR SEQ ID NO:14:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:14:

AAGTCGGTAT TTCACCTAAG      20

( 2 ) INFORMATION FOR SEQ ID NO:15:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:15:

AAGCTTGCAT TGAACTTGTG      20

( 2 ) INFORMATION FOR SEQ ID NO:16:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:16:

GTTTGCCGCC TGCTCTTCCC      20

( 2 ) INFORMATION FOR SEQ ID NO:17:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:17:

GACGGCGATT GAGCCGACGG      20

( 2 ) INFORMATION FOR SEQ ID NO:18:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:18:

TTAGTACCGG TAGTGGCCTG      20

( 2 ) INFORMATION FOR SEQ ID NO:19:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:19:

AAGCTTCCTT GTCAGCGAAA      20

( 2 ) INFORMATION FOR SEQ ID NO:20:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:20:

CAGCGTTTCG TCAGCTTTGC                          20

( 2 ) INFORMATION FOR SEQ ID NO:21:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:21:

CTACGTTATG GTTTACCGGC                          20

( 2 ) INFORMATION FOR SEQ ID NO:22:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:22:

AAGTACGCGA CGGTGTACCG                          20

( 2 ) INFORMATION FOR SEQ ID NO:23:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:23:

GCATCAACCG CAGGTTGCGC                          20

( 2 ) INFORMATION FOR SEQ ID NO:24:

( i ) SEQUENCE CHARACTERISTICS:
    ( A ) LENGTH: 20 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:24:

CACCGGCGTC ACGCAGCGTA                          20

( 2 ) INFORMATION FOR SEQ ID NO:25:

( i ) SEQUENCE CHARACTERISTICS:
    ( A ) LENGTH: 19 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:25:

GATCCGGTAC GCGTGATTT                           19

( 2 ) INFORMATION FOR SEQ ID NO:26:

( i ) SEQUENCE CHARACTERISTICS:
    ( A ) LENGTH: 20 base pairs ( B ) TYPE: nucleic acid
( C ) STRANDEDNESS: single
( D ) TOPOLOGY: linear ( x i ) SEQUENCE DESCRIPTION: SEQ ID NO:26:

CCAGACGCAT AACTCCTCCC 20

( 2 ) INFORMATION FOR SEQ ID NO:27:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:27:

CGCTTGACTC CGTACATGAG 20

( 2 ) INFORMATION FOR SEQ ID NO:28:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:28:

TGGATAGCGT AACCTTACTT 20

( 2 ) INFORMATION FOR SEQ ID NO:29:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:29:

CCACAAGATG CAACCCCGAG 20

( 2 ) INFORMATION FOR SEQ ID NO:30:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:30:

GACGTATCCA TATCATCCTC C 21

( 2 ) INFORMATION FOR SEQ ID NO:31:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:31:

TTGACGATGG ACGCGCTGGA 20

( 2 ) INFORMATION FOR SEQ ID NO:32:

( i ) SEQUENCE CHARACTERISTICS:
( A ) LENGTH: 20 base pairs
( B ) TYPE: nucleic acid
( C ) STRANDEDNESS: single ( D ) TOPOLOGY: linear ( x i ) SEQUENCE DESCRIPTION: SEQ ID NO:32:

CAATTGGTAT AACCAATGTG  20

( 2 ) INFORMATION FOR SEQ ID NO:33:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:33:

AAGCTTCAGC AGTGGCAGAA  20

( 2 ) INFORMATION FOR SEQ ID NO:34:

( i ) SEQUENCE CHARACTERISTICS:
( A ) LENGTH: 21 base pairs
( B ) TYPE: nucleic acid
( C ) STRANDEDNESS: single
( D ) TOPOLOGY: linear ( x i ) SEQUENCE DESCRIPTION: SEQ ID NO:34:

GTATAAACCG CCTTCCGGGC C  21

( 2 ) INFORMATION FOR SEQ ID NO:35:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:35:

CTGCACTGGC GGCGCAAACC  20

( 2 ) INFORMATION FOR SEQ ID NO:36:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:36:

ATAAGACGCG GACAGCGTCG  20

( 2 ) INFORMATION FOR SEQ ID NO:37:

( i ) SEQUENCE CHARACTERISTICS:
( A ) LENGTH: 22 base pairs
( B ) TYPE: nucleic acid
( C ) STRANDEDNESS: single
( D ) TOPOLOGY: linear ( x i ) SEQUENCE DESCRIPTION: SEQ ID NO:37:

AAAGCAAATA AATTTAATTT TT  22

( 2 ) INFORMATION FOR SEQ ID NO:38:

( i ) SEQUENCE CHARACTERISTICS:
( A ) LENGTH: 20 base pairs
( B ) TYPE: nucleic acid
( C ) STRANDEDNESS: single
( D ) TOPOLOGY: linear ( x i ) SEQUENCE DESCRIPTION: SEQ ID NO:38:

GGCCACCCGG CCTTTCGCTG 20

( 2 ) INFORMATION FOR SEQ ID NO:39:

( i ) SEQUENCE CHARACTERISTICS:
        ( A ) LENGTH: 19 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:39:

TCTCGGCGTT GAATGTGGG 19

( 2 ) INFORMATION FOR SEQ ID NO:40:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:40:

CGACGTCTTC CATGGACGGC 20

( 2 ) INFORMATION FOR SEQ ID NO:41:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:41:

GTCAACAAAA TGCAATGGCG 20

( 2 ) INFORMATION FOR SEQ ID NO:42:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:42:

GCGTTATGCT TTTAGTGGCA CTGG 24

( 2 ) INFORMATION FOR SEQ ID NO:43:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:43:

AAGCTTACAC AGCATAACTG 20

( 2 ) INFORMATION FOR SEQ ID NO:44:

( i ) SEQUENCE CHARACTERISTICS:
        ( A ) LENGTH: 22 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:44:

CCAGGCAGGG CATCGGCGGG GG     22

( 2 ) INFORMATION FOR SEQ ID NO:45:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:45:

ATATGAATTC GTCGGCAAGT CCATTCTCCC C     31

( 2 ) INFORMATION FOR SEQ ID NO:46:

( i ) SEQUENCE CHARACTERISTICS:
        ( A ) LENGTH: 31 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:46:

ATATGGATCC GCGGGAGTTA TTCTAGTTGC C     31

( 2 ) INFORMATION FOR SEQ ID NO:47:

( i ) SEQUENCE CHARACTERISTICS:
        ( A ) LENGTH: 87 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:47:

TATAGAATTC CCTTGTCAGC GAAAAAATT AAAGCGCAAG ATTGTTGGTT TTTGCGTGAT     60

GGTGACCGGG CAGCCTAAAG GCTATCC     87

( 2 ) INFORMATION FOR SEQ ID NO:48:

( i ) SEQUENCE CHARACTERISTICS:
        ( A ) LENGTH: 62 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:48:

ATATGGATCC AATCAGCTCC CTGGTTAAGG ATAGCCTTTA GGCTGCCCGG TCACCATCAC     60

GC     62

( 2 ) INFORMATION FOR SEQ ID NO:49:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:49:

CGCCGAATTC GCGGCGTAAT ATATACGTCC CATC     34

( 2 ) INFORMATION FOR SEQ ID NO:50:

( i ) SEQUENCE CHARACTERISTICS:
        ( A ) LENGTH: 42 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:50:

CGCGGGATCC CATGACTCCT TGCTCATCGC ATGAAGACTC CG                                    42

( 2 ) INFORMATION FOR SEQ ID NO:51:

( i ) SEQUENCE CHARACTERISTICS:
    ( A ) LENGTH: 35 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:51:

CGCCGAATTC TGCCGCAGTT TGCGCGCTTT TCCCG                                            35

( 2 ) INFORMATION FOR SEQ ID NO:52:

( i ) SEQUENCE CHARACTERISTICS:
    ( A ) LENGTH: 38 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:52:

GCGCGGATCC GTCATTCTCC TTAAGTTAAC TAACCGG                                          38

( 2 ) INFORMATION FOR SEQ ID NO:53:

( i ) SEQUENCE CHARACTERISTICS:
    ( A ) LENGTH: 82 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:53:

CGCCGAATTC ATCAGAATTT TTTTTCTTTT TCCCCCTTGA AGGGGCGAAG CCTCATCCCC                  60

ATTTCTCTGG TCACCAGCCG GG                                                          82

( 2 ) INFORMATION FOR SEQ ID NO:54:

( i ) SEQUENCE CHARACTERISTICS:
    ( A ) LENGTH: 75 base pairs
    ( B ) TYPE: nucleic acid
    ( C ) STRANDEDNESS: single
    ( D ) TOPOLOGY: linear ( x i ) SEQUENCE DESCRIPTION: SEQ ID NO:54:

GCGCGGATCC CGGAGCTTAC GTGGTTTCCC GGCTGGTGAC CAGAGAAATG GGGATGAGGC                  60

TTCGCCCCTT CAAGG                                                                  75

METHODS AND DIAGNOSTIC KITS FOR DETERMINING TOXICITY UTILIZING BACTERIAL STRESS PROMOTERS FUSED TO REPORTER GENES

CROSS-REFERENCE TO PRIOR APPLICATION

This application is a continuation in part of U.S. application Ser. No. 07/910,793, filed Jul. 6, 1992, now abandoned.

TECHNICAL FIELD OF INVENTION

This invention provides methods and diagnostic kits for determining the toxicity of a compound. The methods and diagnostic kits of this invention employ a plurality of bacterial hosts, each of which harbors a DNA sequence encoding a different stress promoter fused to a gene which encodes an assayable product. Each of these stress promoters is induced by exposure to a different type of cellular stress. The stress promoters utilized in this invention, in toto, comprise those promoter which respond to redox stress, DNA stress, protein stress, energy stress and pH stress. The methods and diagnostic kits of this invention may be employed to characterize and quantify the toxicity of a compound, as well as to identify the cellular mechanism of its toxic action. Moreover, the methods of this invention yield information concerning the action of a compound on a subcellular level. This information may be utilized to design antitoxins to compounds found to be toxic and in active drug design.

BACKGROUND OF THE INVENTION

At least 55,000 chemicals are presently produced in the United States. Over 2,000 new chemicals are introduced into the market each year. Very few of these chemicals have been comprehensively tested for acute or chronic toxicity. For example, less than 1 percent of commercial chemicals have undergone complete health hazard assessment.

The Environmental Protection Agency ("EPA") has the authority to require toxicological testing of a chemical prior to commercial production, but that authority is rarely invoked. Less than 10 percent of new chemicals are subjected to detailed review by the EPA. In the interest of cost and speedy access to the market, the EPA often uses the toxicity of previously tested homologous compounds to gauge the toxicity of a new chemical.

The potential toxicity of new drugs is monitored by the Food and Drug Administration ("FDA"). For a New Drug Application (NDA), the FDA typically requires a large battery of toxicity, carcinogenicity, mutagenicity and reproduction/fertility tests in at least two species of live animals. These tests are required to last up to one year. The costs involved in completing these tests is enormous. For example, a typical 90-day exposure toxicity test in rats costs approximately $100,000. A two year toxicity test in rats costs approximately $800,000 [*Casarett and Doull's Toxicology*, 4th Edition, M. O. Amdur et al., eds. Pergamon Press, New York, New York, p. 37 (1991)].

Besides cost, animal testing also presents disadvantages in terms of time, animal suffering and accuracy. Typical toxicity tests are divided into three stages: acute, short term and long term. Acute tests, which determine the $LD_{50}$ of a compound (the dose at which 50% of test animals are killed), require some 60–100 animals and a battery of tests for determining $LD_{50}$, dose-response curves and for monitoring clinical end points, other than death. Short term tests usually involve at least 24 dogs and 90 rats and last from 90 days in rats to 6–24 months in dogs. Body weight, food consumption, blood, urine and tissue samples are frequently measured in the short-term tests. In addition, dead animals are subjected to post-mortem examinations. Long term tests are similar to short term tests, but last 2 years in rats and up to 7 years in dogs or monkeys.

Animal testing has come under criticism by animal rights activists and the general public because of the severe suffering inflicted on the animals. Moreover, recent evidence calls into question the accuracy of animal testing. For example, variables, such as animal diet, may impair the predictability of animal tests in determining carcinogenic properties [P. H. Abelson, "Diet and Cancer in Humans and Rodents", *Science*, 255, p. 141 (1992)]. And prior determinations on dioxin toxicity, based on guinea pig testing, are now being reevaluated [B. J. Culliton, "U.S. Government Orders New Look At Dioxin", *Nature*, 352, p. 753 (1991); L. Roberts, "More Pieces in the Dioxin Puzzle", *Research News*, October, 1991, p. 377]. It is therefore apparent that there is an urgent need for a quick, inexpensive and reliable alternative to toxicity testing in animals.

Several short-term alternative tests are available. For example, the Ames Assay detects carcinogens which cause genetic reversion of mutant strains of *Salmonella typhimurium*. However, the Ames Assay cannot detect either non-mutagenic carcinogens or non-carcinogenic toxins. The yeast carcinogen assay system described in U.S. Pat. No. 4,997,757 overcomes some of the drawbacks of the Ames Assay, but is still not able to detect non-carcinogenic toxins. Both of these assays are designed to detect alterations and mutations at the DNA level only. Therefore, those prior art tests cannot detect direct damage to proteins or lipid membranes, nor inhibitors of DNA synthesis. Moreover, none of the short-term tests presently employed yields any information about the cellular mechanism by which a carcinogen, mutagen or toxin exerts its effect. Therefore, these prior art assays also do not reveal any information that would be helpful in selecting a counteracting agent or antidote to a compound found to be toxic.

SUMMARY OF THE INVENTION

Applicant has solved the problems set forth above by providing a method which combines a plurality of DNA constructs, each comprising a different stress promoter fused to a DNA sequence which codes for an assayable polypeptide, such as β-galactosidase.

An appropriate bacterial host carrying any one of these fusions is an in vivo diagnostic reagent for determining if a given compound induces the particular stress promoter the strain harbors. By incubating such a host with a given compound and assaying for the detectable polypeptide, one can quickly and easily determine if a particular stress promoter is induced or repressed by the compound. By repeating this procedure with a set of hosts, each harboring a different stress promoter gene fusion, the toxicity of a compound can be both quantified and characterized in terms of how it damages the cell.

The present invention provides such sets of hosts in the form of diagnostic kits for assaying and characterizing toxicity. These kits are optimally designed to determine the toxicity of a compound in a matter of days, rather than the months or years required for animal testing. Furthermore, the kits of this invention achieve these results for a fraction of the cost of animal testing and without the objectionable consequences to live animals. And, the diagnostic kits and methods of this invention yield information about the nature of a toxin's action on the cell—something that the prior art short-term assays fail to do.

The invention also provides a method of identifying an antitoxin to a compound demonstrated to be toxic by the methods of this invention. And the invention provides a method of improving active drug design.

DETAILED DESCRIPTION OF THE INVENTION

Figure 1:
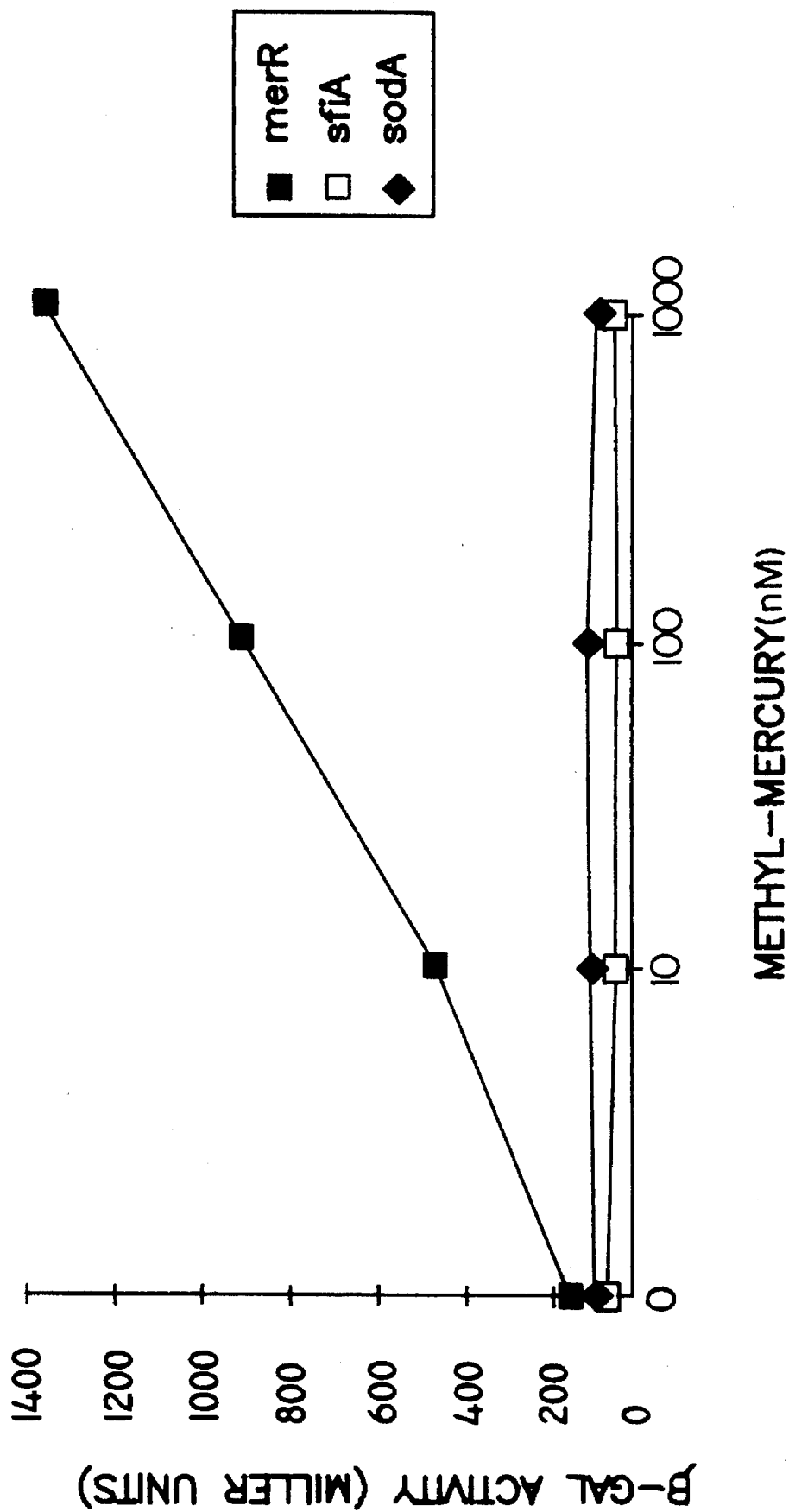
FIG. 1 depicts the induction of the merR, sfiA and sodA promoters by varying concentrations of methyl mercury, as measured by β-galactosidase synthesis.

As used herein, the terms "stress" and "toxicity" are used interchangeably and refer to the disturbance of the biochemical and biophysical homeostasis of the cell.

The term "redox stress", as used throughout this application, refers to conditions which vary from the normal reduction/oxidation potential ("redox") state of the cell. Redox stress includes increased levels of superoxides, increased levels of peroxides—both hydrogen peroxide and organic peroxides—, decreased levels of glutathione and any other conditions which alter the redox potential of the cell, such as exposure to strong reducing agents.

The term "DNA stress", as used herein, refers to alterations to deoxyribonucleic acid or to precursor nucleotides. For example, DNA stress includes, but is not limited to, DNA strand breaks, DNA strand cross-linking, exposure to DNA intercalating agents, both increased and decreased superhelicity, oxidative DNA damage, DNA alkylation, oxidation of nucleotide triphosphates and alkylation of nucleotide triphosphates. The term also includes inhibition of DNA synthesis and replication.

"Protein stress", as used throughout the application, refers to alterations to proteins or individual amino acids, as well as perturbations of intracellular transport of proteins. The term includes, but is not limited to, denaturation of proteins, misfolding of proteins, chelation of protein cofactors, cross-linking of proteins, both oxygen-dependent and -independent oxidation of inter- and intra-chain bonds, such as disulfide bonds, alkylation of proteins, oxidation of individual amino acids and protein damage caused by exposure to heavy metals, such as cadmium.

I use the term "energy stress" to encompass conditions which affect ATP levels in the cell. Examples of energy stress are forced anaerobic metabolism in the presence of oxygen, perturbations of electron transport and exposure to uncoupling agents.

The term "pH stress", as used herein, refers to conditions which cause perturbations in intracellular pH, i.e., which decrease intracellular pH below about 6.0 or increase intracellular pH above about 7.5. pH stress may be caused, for example, by exposure of the cell to ionophores or other cell membrane damaging components, or exposure to weak organic hydrophobic acids, such as phenolic acid. The term also includes cell membrane damage and deleterious changes in electromotive potential.

The term "stress promoter induction" refers to conditions which either increase or decrease the level of expression of assayable gene product.

Individual cells respond to toxic stimuli, in part, by activating specific genes whose protein products detoxify the stimuli or repair damage caused thereby. Mammalian and bacterial cells share a large number of genetic and biochemical responses to damage and stress. For most stress response genes found in mammals, a closely related gene has been identified in bacteria. For example, it has been demonstrated that a bacterial DNA repair enzyme can successfully complement a human cell lacking its own DNA repair enzyme [E. Friedberg, "DNA Repair", *Microbiol. Review*, 52, p. 70 (1988)]. Thus, bacterial responses to stress are reasonably accurate predictors of stress responses in higher eukaryotes.

At least 35 different bacterial stress genes have already been isolated and characterized. These genes are induced by a variety of chemical stresses or cellular damage. Among the chemical stresses which induce one or more of these identified genes are exposure of the cell to mercury, heavy metals, nitroxides, aromatic hydrocarbons, acidity, basicity, alkylating agents, peroxidizing agents, cross-linking agents, ionophores, redox active agents and uncoupling agents. Examples of cellular damage which induce these identified genes are lipid oxidation, DNA strand breaks, DNA alkylation, DNA cross-linking, DNA oxidation, osmotic imbalance, protein oxidation, protein misfolding, protein alkylation, ATP depletion, membrane permeabilization and glutathione depletion. Many more stress genes are believed to exist. The identification and characterization of these additional stress genes is highly desirable in understanding what effects various chemical stresses have on the cell.

The present invention provides diagnostic kits and methods for determining and characterizing the toxicity of a compound in terms of the type of damage it causes within the cell, i.e., DNA damage, protein damage, redox damage, etc. Each diagnostic kit of this invention comprises a plurality of bacterial hosts, each harboring a bacterial stress promoter operatively linked to a gene which codes for an assayable product. That construct may be located in the bacterial chromosome or on an extrachromosomal element, such as a plasmid. Preferqably, the construct is present as a single copy in the bacterial cell chromosome.

The degree of induction or repression of a particular stress promoter is measured by the level of assayable product, as compared to an untreated control culture of the same host. The methods and kits of this invention permit determination of the toxicity of a compound and characterization of the type of cellular damage caused by a compound.

The stress promoters employed in the diagnostic kits and methods of this invention have been chosen based upon the specific types of stress to which the gene they normally regulate responds. Because promoters control gene expression, it is the promoter which is actually induced by stress. Therefore, if the promoter is fused to a gene encoding another polypeptide, the expression of that polypeptide will be affected by exposure to the particular stress which induces the promoter.

Thus, by determining which particular stress promoters are induced by a compound, and comparing those results to standard curves generated by exposure to compounds which are known to cause specific stresses, one can predict and characterize the specific type of cellular stress that compound will cause. This is important both in terms of determining tolerable intake levels of a compound and in predicting symptoms that may be correlated with its toxicity. More importantly, the information that may be obtained by use of the kits and methods of this invention allow for the design of effective antitoxins to a toxic compound, as well as in optimizing new drug design.

The diagnostic kits methods of this invention employ a plurality of bacterial hosts. In toto, these hosts comprise promoters which respond to each of: redox stress, DNA stress, protein stress, energy stress and pH stress.

Preferably, the promoters which respond to redox stress in the methods and kits of this invention are selected from the promoters of the sodA, soi28, katG, ahp, rdc, gsh, zwf and micF genes.

The sodA gene encodes superoxide dismutase and is strongly induced when cells are exposed to chemicals that produce superoxide radicals in the cell, such as paraquat, plumbagin, menadione, streptonigrin, methylene blue and phenazine methyl sulfate [A. Carlioz et al., *EMBO J.*, 5, pp. 623–30 (1986); T. Kogoma et al., *Proc. Natl. Acad. Sci. USA*, 85, pp. 4799–803 (1988); D. Touati, *J. Bacteriol.*, 170, pp. 2511–20 (1988); F. Tsaneva et al., *J. Bacteriol.*, 172, pp. 4197–205 (1990)]. The sodA gene is also induced by metal chelaters, such as 1, 10-phenanthroline, 2,2'dipyridyl and EDTA [D. Touati, supra]. SodA gene induction depends upon an increase in steady state superoxide concentration, not necessarily upon cellular damage caused by superoxides.

The soi28 gene encodes a pyruvate:flavodoxin oxidoreductase. This gene is induced by superoxide-producing reagents only. Specifically, the soi28 gene is induced when two small, thiol-containing proteins—flavodoxin and ferredoxin—become oxidized. These proteins, in reduced form, are required for DNA synthesis. Therefore, severe superoxide stress can cause cessation of DNA synthesis.

The katG gene has been described by P. C. Loewen et al., *J. Bacteriol.*, 162, pp. 661–67 (1985), the disclosure of which is herein incorporated by reference. The katG gene encodes a hydrogen peroxide-inducible catalase activity. It can be induced by $H_2O_2$, specifically, or compounds that cause production of $H_2O_2$ in the cell. The katG gene does not, however, respond to superoxide-generating compounds.

The ahp gene is induced by hydrogen peroxide and organic hydroperoxides, both exogenous and those formed upon peroxidation of proteins and fatty acids. The cloning and sequencing of the ahp gene was described by G. Storz et al., *J. Bacteriol.*, 171, pp. 2049–55 (1989), the disclosure of which is herein incorporated by reference. The ahp promoter-lacZ fusion can be used to distinguish between lipid peroxidation damage and exogenous organic hydroperoxides by cloning the construct into a fatty acid synthesis and degradation mutant of *E. coli*. Such a strain, which is exemplified by a fabB, fadE genotype, can be made to incorporate peroxidation-sensitive fatty acids into its cell membrane by growth on a substrate containing those fatty acids. The induction of ahp promoter-controlled expression of lacZ in such a strain may indicate a compound is causing lipid peroxidation. This can be confirmed by assaying a wild-type strain of *E. coli* which harbors the same construct. Failure of the same compound to induce β-galactosidase expression in this latter strain, confirms that the compound causes lipid peroxidation, but is not itself an organic hydroperoxide.

The rdc promoter is my name for the thiol-sensitive promoter that has been described by G. T. Javor et al., *J. Bacteriol.*, 170, pp. 3291–95 (1988), the disclosure of which is herein incorporated by reference. This promoter is induced by thioglycerol and other strong reductants.

The gsh gene encodes glutathione synthetase and is induced by compounds which deplete cellular glutathione levels, such as N-ethylmaleimide. The gsh gene has been cloned and sequenced [H. Gushima et al., *Nucleic Acids Res.*, 12, pp. 9299–307 (1985), the disclosure of which is herein incorporated by reference].

The zwf gene encodes glucose-6-hydrogenase and is induced by superoxide-producing compounds and nitric oxide [J. T. Greenberg et al., *Proc. Natl. Acad. Sci. USA*, 87, pp. 6181–85 (1990)]. The zwf gene has been cloned and sequenced [D. L. Rowley et al., *J. Bacteriol.*, 173, pp. 968–77 (1991), the disclosure of which is herein incorporated by reference].

The micF gene encodes antisense RNA that shuts off translation of the porin gene, ompF. This gene is induced by superoxide-producing compounds, such as paraquat [J. T. Greenberg et al., supra]. The micF gene is also induced by ethanol and by heat shock. The micF gene has been cloned and sequenced [T. Mizuno et al., *Proc. Natl. Acad. Sci. USA*, 81, pp. 1966–70 (1984), the disclosure of which is herein incorporated by reference].

Other redox stress promoters which can be utilized in the diagnostic kits and methods of this invention include soi17 and soi19, which respond to superoxides [T. Kogoma et al., *Proc. Natl. Acad. Sci USA*, 85, pp. 4799–803 (1988)].

The promoters which respond to DNA stress useful in the methods and kits of this invention are preferably selected from the promoters of the dinD, ada, ada-alkA, leu-500, gyr, top, mutT and nfo genes.

The dinD gene is part of a larger regulon, the SOS regulon, that responds to disruption of DNA replication. Disruption of DNA replication is most often caused by a limited class of DNA lesions, including strand breaks and 'cyclobutane dimers'. Typical inducers of dinD include compounds such as mitomycin C, bleomycin and 4-nitroquinoline oxide, as well as exposure to UV radiation. The dinD promoter does not respond to oxidative DNA damage, except when cells are exposed to extremely high concentrations of $H_2O_2$ (which results in DNA strand breaks). The dinD promoter is also not generally induced by alkylated DNA or oxidatively damaged DNA [S. Kenyon et al., *Nature*, 289, pp. 808–12 (1981)].

The ada gene encodes a protein that responds specifically to alkylated DNA. It, in turn, regulates itself and other genes (alkA and alkB) that are involved in the repair of alkylated DNA. The ada, alkA and alkB genes are all part of the same operon. Alkylation damage to DNA includes production of O-6-alkylguanine and 3-alkyladenine. Known alkylating agents that induce ada gene expression include methlymethanosulfate (MMS), ethlymethanosulfate (EMS) and N-methyl-N'-nitro-N-nitrosoguanidine (MNNG) [B. Demple, *Bioessays*, 6, pp. 157–60 (1987)]. The ada gene has been cloned and sequenced [Y. Nakabeppu et al., *J. Biol. Chem.*, 260, pp. 7281–88 (1985), the disclosure of which is herein incorporated by reference].

The leu-500 promoter is a mutant promoter in the *Salmonella typhimurium* leucine biosynthetic operon. The promoter function can be restored by increasing DNA supercoiling in the cell [D. M. L. Lilley et al., *Molec. Micrbiol.*, 5,. 779–83 (1991)]. Therefore, a leu-500-lacZ fusion inserted into either a *S. typhimurium* or an *E. coli* host can be used to detect agents which cause increased supercoiling.

The gyr gene encodes one of the helicase enzymes in *E. coli*. That enzyme monitors and maintains the correct degree of DNA superhelicity by increasing supercoiling. Agents that decrease superhelicity of the DNA in a cell, such as DNA strand cross-linking agents, induce the gyr promoter [K. Drlica, et al., *Biochemistry*, 27, pp. 2252–59 (1988)].

The top gene encodes a topoisomerase that removes supercoils in overwound DNA [K. Drlica, et al., supra]. Transcription of the top gene is stimulated by treatments that increase superhelicity [Y.-C. Tse-Dinh et al., *J. Mol. Biol.*, 202, pp. 735–42 (1988)]. It therefore responds in a manner opposite that of the gyr gene, which is induced by treatments that decrease supercoiling. In yeast, agents that induce top gene expression also induce recombination, suggesting that recombination is facilitated by topoisomerase. Therefore, I believe that top gene induction may be used to identify 'recombinogenic' agents, which are generally strong carcinogens.

The mutT gene encodes a 15 kilodlaton protein that specifically degrades 8-oxo-dGTP to GMP. 8-oxo-GTP is produced by X-ray irradiation, as well as many naturally occurring oxidants [H. Maki and M. Sekiguchi, *Nature*, 355, p. 273–75 (1992)]. The mutT is induced by agents and conditions that cause cellular production of 8-oxo-dGTP.

The nfo gene encodes a DNA repair enzyme that is specific for oxidative damage. Specifically, that damage is the formation of 3' blocking groups, such as 3' glycolates, formed by the shattering of the imidazole ring of nucleic acids [B. Demple et al., *Proc. Natl. Acad. Sci. USA*, 83, pp. 7731–35 (1986)]. Other DNA repair enzymes do not respond to this type of DNA damage [S. Saporito et al., *J. Bacteriol.*, 170, pp. 5141–45 (1988)]. Nfo is specifically induced by redox active agents, such as paraquat and menadione [S. Farr et al., *Microbiol. Rev.*, 55, pp. 561–85 (1991)].

Other promoters which respond to DNA stress and can be utilized in the methods and kits of this invention include dnaA, which encodes a protein involved in DNA replication and is induced by agents which block replication [C. Kenyon et al., *J. Mol. Biol.*, 160, pp. 445–57 (1982)]; sfiA, which encodes a protein involved in excision repair of DNA and is induced by exposure to UV radiation [P. Quillardet et al., *J. Bacteriol.*, 157, pp. 36–38 (1984)]; nrd, which encodes ribonucleotide reductase, a protein required for DNA synthesis, and is induced by agents which inhibit DNA synthesis [P. Reichard, *Ann. Rev. Biochem.*, 57, pp. 349–74 (1988)]; dinB, whose function is unknown, but is induced by agents which damage DNA [G. C. Walker et al., *J. Mol. Biol.*, 160, pp. 445–57 (1982)]; recA, which is induced by single strand DNA breaks and DNA crosslinking agents [S. Caseragola et al., 185, pp. 430–39 (1982)]; and aidC, which is induced by bulky DNA alkylating agents [R. Fram et al., *Cancer Res.*, 48, pp. 4823–26 (1988)].

The promoters which respond to protein stress useful in the methods and kits of this invention are selected from rpoD, lon, clpB, merR, fepB-entC, meto and groE genes.

The rpoD gene encodes a sigma subunit that is part of the RNA polymerase holoenzyme. The rpoD promoter is a strong "heat shock" promoter that responds to all of the same conditions that induce the heat shock response [D. W. Cowing et al., *Proc. Natl. Acad. Sci. USA*, 82, pp. 2679–83 (1985)]. In addition to increased temperature, the "heat shock" response is also induced by almost all alcohols, as well as some heavy metals. The cellular response to "heat shock" is actually a response to an increase in the concentrations of misfolded mature proteins and unfolded nascent proteins.

The lon gene encodes an ATP-dependent protease which digests misfolded proteins [D. T. Chin et al., *J. Biol. Chem.*, 263, pp. 11718–28 (1988)]. It responds to agents which cause misfolding of mature proteins.

The clpB gene product has protease activity and can bind to damaged proteins. It is induced when the cell produces an abundance of damaged proteins [M. Kitigawa et al., *J. Bacteriol.*, 173, 4247–53 (1991)]. Misfolded or truncated proteins induce clpB gene expression.

The merR gene responds to elemental mercury, as well as most inorganic mercury compounds [W. Ross et al., *J. Bacteriol.*, 171, pp. 4009–18 (1988)]. Mercury is known to cause modification of thiol groups of proteins, frequently leading to inhibition of enzyme function. Mercury can also alter sulphydryl groups in cell membranes, causing changes in membrane permeability and membrane transport.

The fepB-entC gene encodes a periplasmic protein required for iron transport into the cell. Expression of fepB-entC is regulated by the amount of available iron within the cell. Low iron levels induce the gene, while high levels shut off its transcription [T. J. Brickman et al., *J. Mol. Biol.*, 212, pp. 669–82 (1990)].

The meto gene encodes methionine sulfoxide reductase. The gene is induced by oxidized methionine.

The groE gene plays a role in cell growth. Although the product of the groE gene has ATPase activity, its cellular function is not yet understood. It is also known that the groE gene product functions as a molecular chaperon protein. The groE gene is induced by agents which cause protein misfolding [D. W. Cowing et al., *Proc. Natl. Acad. Sci. USA*, 82, pp. 2679–83 (1985)]. The sequence of the groE promoter has been reported [D. W. Cowing et al, *J. Mol. Biol.*, 210, pp. 513–20 (1989), the disclosure of which is herein incorporated by reference].

Other promoters which respond to protein stress and can be utilized in the methods and kits of this invention include dnaK, which is induced by agents which cause misfolding of proteins [D. W. Cowing et al., *Proc. Natl. Acad. Sci. USA*, 82, pp. 2679–83 (1985)]; and rimK, which is believed to be induced by agents which inhibit or disrupt translation [W. Kang et al., *Molec. Gen. Genetics,* 217, pp. 281–88 (1989)].

The promoters which respond to energy stress useful in the methods and kits of this invention are selected from the promoters of the sdh, cyo, cyd and unc genes.

The sdh gene encodes succinate dehydrogenase, an enzyme that removes electrons from succinate and donates them to cytochrome oxidase [R. Poole and W. Engledew, in "Escherichia coli and Salmonella typhimurium", F. C. Neidhardt, ed., ASM Press, Washington, D.C., pp. 170–200 (1987)]. Expression of the sdh gene is regulated by the presence of oxygen in the cell. Under anaerobic conditions or conditions which disrupt electron transport, the sdh gene is turned off. Thus, the expression of β-galactosidase regulated by an sdh-lacZ fusion would decrease in the presence of a toxin which affects electron transport.

The cyo and cyd genes encodes the two cytochrome oxidase genes in *E. coli*. The cyo gene is expressed strongly when cells are growing under normal aerobic conditions, but is repressed under anaerobic conditions or conditions that inhibit respiration [S. Iuchi et al., *J. Bacteriol.*, 172, pp. 6020–6025 (1990)]. Therefore, like the sdh fusion described above, it is decreased cyo promoter-controlled expression of assayable product that indicates a compound is toxic. The cyd gene, in contrast, is induced under conditions which inhibit respiration and repressed under normal, aerobic growth conditions.

The unc gene encodes one of the F1-ATPase subunits. It is induced by agents that reduce the energy charge (ATP level) of the cell such as uncoupling agents and ionophores [K. von Meyenberg et al., *EMBO J.*, 4, pp. 2357–63 (1985)].

Promoters which respond to pH stress useful in the methods and kits of this invention are selected from the promoters of the hag, katF, micF and aniG genes.

The hag gene encodes a protein involved in cell mobility. Cell mobility requires a proton gradient across the cell membrane to a flagellar motor [M. J. Silverman et al., *J. Bacteriol.*, 120, pp. 1196–1203 (1974)]. Any compound that disrupts the pH gradient by allowing a free flow of ions across the membrane will induce hag gene expression and thus, the hag promoter.

The katF gene encodes a regulator of one of the two catalases in *E. coli* [Triggs-Raine and Loewen, *Gene,* 52, pp. 121–28 (1987)]. It is induced by conditions that change the intracellular pH, such as exposure to weak organic acids like phenolic acid. It is also induced by starvation.

The micF gene, which is described above in the redox stress promoter section, also responds to both membrane damage and changes in osmotic pressure [J. T. Greenberg et al., *Proc. Natl. Acad. Sci. USA*, supra]. Both ethanol and heat shock are known to induce the micF gene.

The aniG gene is a *S. typhimurium* gene that is induced by changes in intracellular pH [Z. Aliabadi et al., *J. Bacteriol.*, 170, pp. 842–51 (1988)]. The aniG promoter may be employed in the kits and methods of this invention in either a *S. typhimurium* host or in an *E. coli* host.

Other promoters which respond to pH stress and which may be employed in the kits and methods of the present invention include cps, which encodes capsular polysaccharide synthetase gene and is induced by cell membrane damage [S. Gottesman et al., *Molec. Microbiol.*, 5, pp. 1599–606 (1991)]; proU [A. Barron et al., *J. Bacteriol.*, 167, pp. 433–38 (1986)], which is induced by increases in osmotic pressure; and mdoA, which encodes an enzyme involved in the synthesis of periplasmic membrane oligosaccharides and is induced by membrane damage and osmotic stress [J. M. Lacroix et al., *Molec. Microbiol.*, 5, pp. 1745–53 (1991)].

In addition to those promoters described above, new stress promoters that may be discovered and characterized may also be employed in the methods and kits of this invention.

To identify new stress promoters one may prepare and screen a Mu dX phage chromosomal or plasmid library. The preparation of such libraries is described by T. A. Baker et al., *J. Bacteriol.*, 156, pp. 970–74 (1983), the disclosure of which is incorporated by reference.

A chromosomal library is created by transfecting an ampicillin-sensitive bacterial strain, preferably *E. coli* which lacks the entire lac operon, with Mu dX. This phage, which carries the lacZ gene, randomly inserts into the host chromosome. Certain of those insertions produce a stress promoter-lacZ fusion. To identify those fusions, ampicillin-resistant transfectants are screened for induction of β-galactosidase expression by known inducers of particular stresses.

A plasmid Mu dX library is constructed by isolating the chromosomal DNA of a lac⁻ bacterial host, preferably *E. coli*, and subjecting it to restriction digestion. The resulting chromosomal fragments, some of which will contain all or a portion of a stress gene and its promoter, are then cloned into a similarly digested vector, which does not carry an ampicillin resistance gene, but preferably carries another antibiotic resistance gene, i.e., tetracycline. resistance. An example of such a vector is pKT328. The resulting plasmid library is then used to transform an $amp^S$, $tet^S$, lac⁻ bacterial strain $Amp^R$, $tet^R$ transformants are isolated and are then transfected with Mu dX phage. The transfectants are grown in media containing ampicillin and tetracycline. Plasmid DNA is then isolated and used to transform an $amp^S$, $tet^S$, lac⁻ bacterial strain. Screening for fusions is achieved as described above, except that the desired transformants are both $amp^R$ and $tet^R$.

The plasmid library method is preferable because it allows detection of Mu dX insertions into stress genes that might otherwise be lethal. Only the plasmid copy of the stress gene contains the Mu dX insertion. Thus, the chromosomal copy of the stress gene is still functional and is able to respond to the stress.

Another method of identifying new stress promoters and creating fusions to DNA encoding assayable proteins involves the insertion of random restriction fragments of bacterial chromosomal DNA into specially designed vectors. Such vectors contain a multiple cloning site situated 5' to a DNA sequence which codes for an assayable protein. The most preferred vector of this type is pRS415. Following the shotgun insertion of bacterial chromosomal fragments into such a vector, the resulting recombinant DNA molecule is used to transform a strain of bacteria that lacks the entire lac operon, but is wild type in every other aspect. The resulting transformants are screened with compounds that cause known stresses. Those transformants that have altered expression of the assayable protein in the presence of such compounds contain desirable fusions.

The diagnostic kits and methods of this invention rely on the induction of specific stress promoters to alter expression of an assayable gene product. This change in expression level is measured both qualitatively and quantitatively. In order to be useful in those kits and methods, the particular stress promoter must be operably linked to the gene which encodes an assayable product. The term "operative linkage" refers to the positioning of the promoter relative to the gene encoding the assayable product such that transcription of the gene is regulated by the promoter. Such positioning is well known in the art and involves positioning the promoter upstream (5') of the gene so that no transcription termination signals are present between the promoter and the Shine-Dalgarno site preceding the gene.

Preferably, the piece of DNA carrying the carrying the gene encoding the assayable product will also contain that gene's Shine-Dalgarno sequence and translation start codon. In this manner, proper reading frame is not an issue when the DNA carrying the stress promoter is ligated to the DNA encoding the assayable product. This is true even if the promoter DNA also carries a Shine-Dalgarno sequence and a portion of the stress gene coding region. For such constructs, sufficient translation will be controlled by the Shine-Dalgarno sequence of the assayable product gene and initiate at that gene's start codon to detect induction of the promoter.

Also within the scope of this invention are constructs wherein the assayable gene product is a fusion protein, containing an N-terminal portion of the native stress gene product. In these constructs the piece of DNA containing the promoter also contains DNA encoding at least the N-terminal amino acid of the stress gene product. Such constructs are useful in detecting stresses that affect gene expression at the translational level. For these constructions, operative linkage requires ligating the 5' end of the DNA encoding the assayable product to the 3' end of the DNA containing the promoter and part of the stress gene coding region such that the DNA encoding the N-terminal amino acids of the stress gene product are in the same reading frame as the DNA encoding the assayable product. It will be apparent to those of ordinary skill in the art that for such constructs the promoter DNA will contain the Shine-Dalgarno sequence and translational start codon and that the DNA encoding the assayable product must not contain its own Shine-Dalgarno sequence.

The choice of genes to operably link to the stress promoters in the kits and methods of this invention is essentially limitless, as long as (1) a DNA sequence encoding the assayable product has been characterized; and (2) the product of the gene can be detected. Sufficient characterization includes knowledge of the entire coding sequence, availability of a cDNA molecule or knowledge of a sufficient number of restriction sites within the DNA sequence to allow the gene to be manipulated so as to create an operative linkage to the stress promoter.

Preferably, the assayable product is β-galactosidase (encoded by the lacZ gene), chloramphenicol acetyl transferase (encoded by the cat gene), galactose kinase (encoded by the galK gene), β-glucosidase (encoded by the gus gene), glutathione transferase or luciferase (encoded by the lux gene). Most preferably, the lacZ gene is employed.

The stress promoter-assayable product fusions harbored by the hosts employed in the diagnostic kits and methods of this invention may be made using standard recombinant DNA techniques that are well known in the art. The choice of techniques depends upon what is known about the particular stress promoter to be used in the strain. If a stress gene has been cloned onto a plasmid, the Mu dX insertion technique described above may be utilized to form a stress promoter-assayable gene product fusion. The only requirement for using Mu dX in this instance is that the plasmid harboring the stress gene not encode ampicillin resistance. Screening for a functional fusion is achieved by exposing transfectants to a stress which is known to induce the specific stress gene. For any of the above Mu dX transfection protocols it is preferable that the bacterial strain which is exposed to the stress have a wild-type phenotype for all genes other than lac. An example of a strain that is preferable for harboring a stress promoter-assayable product fusion is E. coli strain SF1.

If the nucleotide sequence of the stress gene is known, polymerase chain reaction technology may be employed to produce lacZ or other assayable protein fusions. Specifically, one synthesizes primers which are complementary to the 5' and 3' ends of the stress promoter portion of the gene, hybridizes those primers to denatured, total bacterial DNA under appropriate conditions and performs PCR. In this manner, clonable quantities of any sequenced stress promoter may be obtained. Once the stress promoter DNA has been obtained, it is ligated to a DNA encoding an assayable protein in an appropriate vector, such as pRS415, which contains a multiple cloning site just upstream from the lacZ gene [R. Simons et al., Gene, pp. 85–96 (1987)]. Such methods are well-known in the art.

The choice of bacterial strain to ultimately harbor the particular stress promoter-assayable product construct and thus useful in the methods and kits of this invention is only limited by the strain's inability to synthesize the assayable product in its untransformed state. Most preferably, the strain used should be homologous with the stress promoter. The strain should also be wild type for all other genes, especially stress genes. In this manner, there exists a chromosomal version of the host stress gene that can properly respond to a stress, in addition to another copy of the stress promoter which is induced to produce the assayable product. The preferred strain is E. coli SF1, which was created by the inventor and is described below.

In order to compare the level of induction of various stress promoters in the kits and methods of this invention, it is desirable that the copy number of each stress promoter-reporter gene fusion utilized in the kits and methods of this invention be equal. Because plasmids harboring these fusions can vary widely in the number of copies per cell, the most preferable method for equalizing copy numbers is to integrate the stress promoter-reporter gene construct into the bacterial chromosome. In this manner, each fusion will be present in a single copy.

The most preferred method of achieving integration into the bacterial chromosome is through the use of a bacteriophage. Any phage that contains two or more different regions of DNA homologous with two segments of DNA on the vector containing the fusion can be employed. These dual regions of homology allow a double recombination event to occur between the vector and the phage when the phage infects a cell harboring the vector. This allows the vector to integrate into the phage genome. An example of such a bacteriophage is λRS88, a lytic-defective phage which contains regions of DNA homologous to the ampicillin resistance gene and to β-galactosidase.

Phage containing the integrated fusion are identified by assaying plaques for reporter gene expression following inoculation onto a lawn of bacteria in the presence of a compound that induces the particular stress gene in the fusion. Positive plaques are then isolated and phage therein used to infect bacteria under lysogenic conditions. Most preferably, the phage employed in this process are lytic defective, i.e., the phage DNA cannot jump out of the bacterial chromosome under conditions which normally induce the lytic cycle.

It is preferable that each bacterial host employed in the kits and methods of this invention harbors only one particular stress promoter-assayable gene product fusion. In this manner, if a compound induces expression of the assayable gene product in any particular host, the specific type of stress caused by the compound can unambiguously be identified. It should be understood, however, that certain stress promoters that may be employed in methods and kits of this invention can respond to more than one type of stress. For example, the sodA promoter is induced by both superoxides and by metal chelaters.

When a promoter which responds to multiple types of stress is employed in the kits and methods of this invention, it is preferable that a host harboring another promoter, which responds to only one of those stresses, is also employed. In this manner, the nature of the stress caused by the compound can be more accurately determined. Thus, the use of an *E. coli* host harboring a soi28 promoter-assayable gene product fusion, which responds solely to superoxides, may be used together with a host harboring the sodA promoter fusion. This combination of hosts allows one to determine whether induction of the latter promoter was due to superoxide formation or metal chelation. According to the most preferred embodiment, the kits and methods of this invention employ the following promoters fused to β-galactosidase: soi28, dinD, hag, ada, gyr, katG, nfo, clpB, merR, top, cyd, micF, zwf, groE, katF and aniG. Each of the stress promoter fusions is present as a single copy integrated into the bacterial chromosome of a different host. All of the fusions except for aniG are preferably in *E. coli* strain SF1. The aniG fusion is preferably in a strain of *S. typhimurium*.

It is known that some compounds are not toxic to mammals in their native form, but become toxic after being processed by the liver. Therefore, according to another embodiment of this invention, the compound to be tested in the methods and kits of this invention is pre-treated with an S9 liver extract. Methods for preparing an S9 liver extract ("S9") are described by S. Vennitt et al., In *Mutagenicity Testing—A Practical Approach*, S. Vennitt et al., eds., IRL Press, Oxford, England, pp. 52–57 (1984), the disclosure of which is herein incorporated by reference. S9 is essentially a crude homogenate of rat liver with insoluble particles removed by low speed centrifugation. S9 is incubated with the test compound in a potassium buffer containing NADP to mimic stage I and stage II biotransformation of compounds normally performed by the mammalian liver.

Prior to carrying out an assay on a compound of unknown toxicity using the methods and kits of this invention, standard curves are preferably generated utilizing at least one and preferably three compounds that are known to induce each specific stress promoter that will be used to screen the unknown compound. Each known chemical should more preferably be tested against all of the promoters, not just the promoter that it is known to induce. And each chemical should be assayed over a sufficiently wide range of concentrations to provide a useful standard curve, preferably 1 picomolar to 1 millimolar.

Once the standard curves have been generated, a computer data base containing those curves is generated. This database is then used to compare stress promoter-induction profiles of the compounds to be tested with those of the toxins used to generate the standard curve. Thus, the results for any untested compound are expressed in terms of relative toxicity compared to known inducers of stress promoters.

Each of the characterization and toxicity determination methods of this invention comprise the first step of separately culturing each of the individual bacterial hosts described above. The hosts should be grown so that they are in log or stationary phase. Growth may be in a minimal media, such as M9 supplemented with glucose, or in LB; with or without antibiotics, such as ampicillin or tetracycline, depending on the strain of bacteria used. Growth temperatures of between 30° C. and 37° C. may be employed, with the lower end of the range being preferred if the stress promoter-assayable product fusion was achieved via temperature-sensitive phage transfection, such as Mu dX. Growth of the hosts is followed by measuring cell density via absorbance of the culture at 600 nm ($OD_{600}$). An $OD_{600}$ of between about 0.1 and 0.2 is most preferable.

Following this initial growth, the compound to be tested is added to a portion of each culture. For initial tests, a series of 10-fold dilutions of the compound should be used, ranging from millimolar to picomolar concentrations. Another series of dilutions of the compound which have been pre-incubated with S9 fraction should also be prepared and added to a second portion of each culture. A third portion of each culture is not exposed to the compound and is used as both a control to measure the effect of the compound on the overall growth of the cells and for a baseline measurement of assayable gene product. The $OD_{600}$ of the cultures just prior to exposure to the compound is recorded.

All of the cultures (both control and exposed) are then allowed to incubate at normal growth temperature for a period of time ranging from 5 minutes to 24 hours. More preferably, exposure to the toxic or test compound is for about 2 to 4 hours. After this additional incubation, a portion of both the exposed and control cultures is used to determine comparative growth by measuring $OD_{600}$. Another portion of both the control and exposed culture is used to measure the level of assayable gene product. Those of skill in the art are well aware that if the assayable product is cytoplasmically located, the hosts must be lysed prior to performing the particular assay. Methods for lysing bacteria are well known in the art and include mechanical methods, such as homogenization; enzymatic methods, such as treatment with lysozyme; and cell wall solubilization methods, such as treatment with toluene or chloroform. If, on the other hand, the assayable product is secreted out of the host cell, only the culture fluid need be used for the assay.

once the assayable product is released from the cells it can be quantified. Quantification may be carried out in a number of ways that are well known in the art. For example, a colorimetric substrate may be utilized if the expression product is an enzyme. Appropriate colorimetric substrates for specific enzymes are well-known in the art. Alternatively, an assay which employs specific antibodies, such as an RIA or ELISA, can be used to detect the expression product. Even assays which detect mRNA levels, such as Northern blots, may be employed to detect induction. In the most preferred embodiment, the expression product, β-galactosidase, is assayed for by employing the colorimetric substrate, o-nitrophenyl galactose (ONPG). The reaction is quantified spectrophotometrically by measuring absorbance at 420 and 550 nm.

Depending upon the nature of the assay used, the buffer conditions of the lysed culture or supernatant may need to be adjusted. Accordingly, suitable buffer may be added to the lysed culture or supernatant so that optimal conditions for the particular assay are obtained. For example, if the assayable product is to be detected by an RIA or ELISA assay, the buffer conditions must be adjusted to a neutral pH to allow for maximal antibody-antigen complex formation and to minimize non-specific antibody binding. Such conditions are well known in the art and are exemplified by a final buffer condition of 50 mM phosphate buffer, 150 mM NaCl, pH 7.0. If the assayable product is an enzyme and detection is to be achieved by a colorimetric substrate assay, buffer conditions must be optimized for maximal enzymatic activity and minimal non-catalytic cleavage of the substrate. These conditions are conventional and vary depending on the enzyme to be assayed.

For assays which utilize colorimetric substrates to measure directly enzymatic expression product (as opposed to ELISA assays which indirectly utilize colorimetric substrates), the time of the reaction must be recorded, because time is an element for measuring activity. In such assays, it is therefore not necessary to stop the reaction between expression product and colorimetric substrate in all cultures simultaneously. Obviously, however, the reaction in any particular control sample will be stopped at the same time as the corresponding test sample. Those of skill in the art are aware of how to stop the various enzyme/substrate reactions. Even more preferably, the reaction in multiple samples is monitored simultaneously through the use of a device, such as a multi-well plate reader. When utilizing such a device, a curve plotting adsorbance versus time is generated. Reporter gene product activity is then expressed as the change in adsorbance over time, i.e., the slope of the linear portion of the generated curve. The use of this preferred method of measuring reporter gene product activity avoids the need for stopping the colorimetric reaction.

According to the most preferred embodiment of this invention, the assayable product is β-galactosidase, the host cells are lysed by the addition of chloroform and the buffer conditions for the assay are 0.06M $Na_2HPO_4$—$7H_2O$, 0.04M $NaH_2PO_4$—$H_2O$, 0.01M KCl, 0.001M $MgSO_4$—$H_2O$, 0.05M β-mercaptoethanol, pH 7.0. If necessary, the reaction is preferably stopped by the addition of $Na_2CO_3$.

The data gathered from the above-described measurements allows one to plot test compound concentration versus cell growth ($OD_{600}$ measurements) and test compound concentration versus level of stress promoter induction (as determined by the amount or rate of assayable product produced).

The former plot is important because exposure of certain of the transformed hosts utilized in the kits and methods of this invention to high concentrations of test compounds may be lethal. Thus, an accurate reading of specific induction of a stress promoter cannot be obtained for that concentration of test compound. If, however, cell death occurs without a concomitant induction of a particular stress promoter, it is apparent that the test compound is toxic, but does not cause that particular stress. This may indicate that additional fusions should be tested against the test compound.

It is known that while individual compounds may not be toxic, combinations of non-toxic compounds may, in fact be toxic. Therefore, it should be understood that the kits and methods of this invention can also be utilized to determine the potential toxicity of combinations of known and unknown compounds in an identical manner to that described above.

According to another embodiment, the invention provides a method of identifying an antitoxin to a compound determined to be toxic by the methods of this invention. As described above, once a stress promoter induction/suppression profile is generated for an unknown compound, that profile is compared to profiles of known compounds in a database. A potential antitoxin to the unknown compound is a known antidote to a compound having a similar stress promoter induction/suppression profile. In order to test the efficacy of such an antitoxin, the stress promoter assay is repeated using only those hosts containing stress promoters which were induced or suppressed by the unknown compound. Each of those hosts is pre-incubated with varying concentrations of the proposed antitoxin prior to the addition of an inducing/suppressing concentration of unknown compound. If pre-incubation with the proposed antitoxin decreases or obliterates the effect of the unknown compound, such an antitoxin will likely be effective.

Finally, this invention provides a method of improving active drug design. According to this embodiment, a new drug is first tested with any of the above-described kits and methods and its toxicity is determined. The information provided by such methods and kits indicates the cellular mechanism of the drug's toxicity. The portion of the drug that is likely to cause the particular cellular damage indicated may then be appropriately modified or eliminated depending upon the role that portion plays in the drug's pharmaceutical activity. The resulting modified drug is then retested with the kits and methods of this invention to determine if its toxicity has been sufficiently reduced or eliminated. Drugs improved and modified by this method are also within the scope of this invention.

In order that the invention described herein may be more fully understood, the following examples are set forth. It should be understood that these examples are for illustrative purposes only and are not to be construed as limiting this invention in any manner.

Certain of the basic molecular biology techniques described below are not set forth in detail. Such techniques are well known in the art and are described in the disclosure of *Molecular Cloning—A Laboratory Manual Second Edition*, J. Sambrook et al., eds., Cold Spring Harbor Laboratory Press, New York (1989), the disclosure of which is herein incorporated by reference.

EXAMPLE 1

Use of Phage Mu dX to Create Stress Promoter-lacZ Fusions

The Mu dX phage carries the ampicillin resistance gene and both the lacZ and lacY genes. The phage makes random insertions into genes or operons in such a way that in some transductants, the lacZ and lacY genes it carries are placed under control of a promoter of the gene or operon in which the insertion lies. Some of these productive insertions will occur in stress-inducible genes. Such insertions were selected for by assaying for ampicillin resistant transductants that increase or decrease expression of lacZ under conditions which induce the stress promoter. Because the Mu dX phage is somewhat temperature sensitive, all cultures were grown at 30° C., instead of 37° C.

I. Preparation of Mu dX Lysate

To prepare the Mu dX lysate, I used the method described by J. H. Krueger et al., *Meth. Enzymol.*, 100, pp. 501–09 (1983), the disclosure of which is herein incorporated by reference. Specifically, I grew *E. coli* MAL103 cells, which contain both the Mu dX bacteriophage and an MuC temperature-sensitive helper bacteriophage inserted in its chromosome, in LB+ampicillin (70 µg/ml) at 28° C. until they reached a density of $10^8$ cells/ml. I then shifted the growth temperature to 43° C. for 20 minutes and back to 37° C. for 60 minutes or until lysis was apparent. I then added 1% v/v chloroform and incubated the culture for an additional 5 minutes at room temperature. The culture was then centrifuged at 8,000 rpm for 5 minutes, the supernatant was saved in a sterile tube and the pellet was resuspended in fresh LB. The suspension was centrifuged once again at 8,000 rpm for 5 minutes and the resulting supernatant was added to the initial supernatant and stored at 4° C. in 1% v/v chloroform.

II. Use of Mu dX to Create a lacZ Fusion with a Known stress Promoter

When a stress gene ha already been identified and cloned onto a plasmid, I used the following techniques to create a stress promoter-lacZ fusion. First, the E. coli strain carrying the plasmid must be $Amp^S$ and the plasmid should preferably contain a drug resistance marker other than $Amp^R$. I grew the cells carrying the plasmid in LB at 30° C. to a concentration of $10^9$ cells/ml. I then centrifuged the cells and resuspended the pellet in ½ of the original volume of LB. I added $CaCl_2$ to a final concentration of 2.5 mM and stored the cells on ice.

I next made a series of 4 ten-fold dilutions of the phage lysate described in part I, above, into 25 mM $MgSO_4$, 1 mM $CaCl_2$. I then mixed 100 µl of each phage dilution with 100 µl of the E. coli cells and incubated at 30° C. for 20 minutes. The cells were then centrifuged and the supernatant was discarded. The pellet was resuspended in 2 ml of LB and incubated at 30° C. for 100 minutes. I then added chloramphenicol to the cultures (15 µg/ml final concentration) and incubated for an additional 3 hours at 30° C. I next performed a plasmid mini-prep. The resulting plasmids were then used to transform a lac⁻, $Amp^S$ E. coli strain using a CELL-PORATOR (electroporation apparatus) [BRL, Bethesda, Md.] and following the manufacturer's directions. The transformants were plated onto LB+ampicillin (70 µg/ml)+X-gal (40 µg/ml) plates which, if the original plasmid contained an antibiotic resistance gene, also optionally contained the appropriate antibiotic. After growing the transformants overnight at 30° C., I picked 100 blue colonies and replated them on duplicate plates containing the same media, one of which additionally contained an agent that induces or represses the particular stress gene contained on the plasmid.

If the added agent caused induction of the stress gene, those colonies which were darker blue on the plate containing inducing agent were assumed to contain a fusion between the lacZ gene and the promoter of the cloned stress gene. Conversely, if the agent represses the stress gene, those colonies that were significantly lighter blue in color or white on the agent-containing plate were selected as harboring the desired construct. Confirmation of such constructs was achieved using the β-galactosidase assay described below.

III. Use of Mu dX to Create a Library Containing lacZ Fusions with Unknown Stress Promoters The two methodologies described below allowed me to discover heretofore unknown stress promoters.

A. Chromosomal Libraries

I infected an exponentially growing culture of an E. coli strain that lacked the entire lac operon with phage Mu dX at a multiplicity of infection of 0.1–0.2, as described above in part II. The transductants were selected by growth on LB+ampicillin (70 µg/ml) plates at 30° C. I then replica plated the transductants onto LB+X-gal (40 µg/ml) plates in either the presence or absence of an, agent which induces a defined stress and incubated the plates overnight at 30° C. Colonies that differed significantly in color intensity in the presence of the agent as compared to its absence were selected.

Cultures of those selected colonies were then assayed for the inducibility or repression of β-galactosidase activity as described below.

B. Plasmid Libraries

This methodology is similar to the one above, but avoids any potential lethality caused by the insertion of the Mu dX phage into a stress gene, thereby inactivating that gene.

Specifically, plasmid pKT218 ($Amp^S$, $Tet^R$) is completely digested with PstI, which cuts at a single site in the plasmid. The sample is then inactivated with phenol/chloroform and the DNA precipitated using sodium acetate/EtOH. The vector is then treated with bacterial alkaline phosphatase to prevent self-annealing.

Genomic DNA is isolated from a strain of E. coli that lacks the entire lac operon, but is wild type in every other aspect. The isolated DNA is then partially digested with PstI. Following digestion, the sample is treated with phenol/chloroform to inactivate the enzyme. The restricted DNA is then precipitated using the sodium acetate/EtOH method.

The digested chromosomal DNA is then ligated to the correspondingly digested vector. The ligation mixture is used to transform competent E. coli lac⁻ cells by electroporation. Transformants are grown in LB+tetracycline at 30° C. until they reach stationary phase. Chloramphenicol (15 µg/ml final concentration) is then added and the culture is incubated for an additional 3 hours at 30° C. Plasmids are then isolated from the culture and used to transform a lac⁻, $Tet^S$ strain using the electroporation technique. The transformants are then grown in LB+tetracycline until they reach log phase.

The transformants are then infected with Mu dX at a multiplicity of infection of 0.1–0.2, as described above. The transductants are then plated onto LB+ampicillin (70 µg/ml)+tetracycline plates and grown overnight at 30° C. Individual colonies are then replica plated onto X-gal (40 µg/ml) plates in either the presence or absence of an agent which induces a defined stress and the plates are incubated overnight at 30° C. Colonies that differ significantly in color in the presence of the agent, as compared to its absence are selected.

Cultures of those colonies were then assayed for the inducibility or repression of β-galactosidase as described below.

EXAMPLE 2

Use of pRS415 to Create Stress Promoter-LacZ Fusions

I. Use of pRS415 to Create a Stress Promoter-LacZ Fusion with an Unknown Stress Promoter The plasmid pRS415 contains the lacZ gene and a multiple cloning site just upstream from that gene. It is described in R. Simons et al., *Gene*, pp. 85–96 (1987), the disclosure of which is herein incorporated by reference.

The SmaI site in pRS415 allows for shotgun cloning of chromosomal DNA that is cut with any restriction enzyme and then blunt-ended with exonuclease. All of the techniques described below are standard protocols in the molecular biology art and are described in *Molecular Cloning—A Laboratory Manual Second Edition*, J. Sambrook et al., eds., Cold Spring Harbor Laboratory Press, New York (1989).

Specifically, genomic DNA is isolated from a strain of *E. coli* that lacks the entire lac operon, but is wild type in every other aspect. The isolated DNA is then partially digested with any restriction enzyme which cuts at a four base pair target. Following digestion, the samples are treated with phenol/chloroform to inactivate the enzymes. The restricted DNA is then precipitated using the sodium acetate/EtOH method. If necessary, the sample is then digested with S1 nuclease to create blunt ends and then reprecipitated with sodium acetate/EtOH.

Simultaneously, pRS415 is digested with SmaI. The sample is then inactivated with phenol/chloroform and the DNA precipitated using sodium acetate/EtOH. The vector is then treated with bacterial alkaline phosphatase to prevent self-annealing.

The digested chromosomal DNA is then ligated to the correspondingly digested vector. The ligation mixture is used to transform competent *E. coli* lac⁻ cells by electroporation using a CELL-PORATOR apparatus. Following transformation, the transformants are diluted and plated on LB+ampicillin (70 µg/ml)+tetracycline+X-gal (40 µg/ml) plates at a density of 1000 colonies per plate. After growing overnight at 37° C., replica plates of the above plates are made onto two plates of the same medium, one with and one without the addition of a compound which produces a desired stress. Transformants containing inserted, inducible promoters in the pRS415 vector will be darker blue on the stress compound-containing plate than on the control plate. Conversely, transformants containing lacZ fusions to a promoter which is repressed by stress will be lighter blue or white on the compound-containing plate.

Inducibility or repression is confirmed with individual positive clones using one of the β-galactosidase assays described below and varying concentrations of the stress-inducing compound.

II. Use of pRS415 to Create a Stress Promoter-LacZ Fusion with a Known Stress Promoter A. Creation of a Known Stress Promoter DNA Fragment Using PCR Amplification When the sequence of a stress gene is available and the promoter region has been located, I employ a PCR protocol to amplify the stress promoter. Specifically, I design a pair of primers that is complementary to the 5' and 3' ends of the stress promoter. The region to be amplified is normally in the range of 300 to 800 base pairs and the length of the primers ranges from about 15 to 25 nucleotides.

Once the primers are synthesized, they are hybridized to genomic DNA utilizing well-known PCR conditions [see for example, *Molecular Cloning—A Laboratory Manual Second Edition*, J. Sambrook et al., eds., Cold Spring Harbor Laboratory Press, New York (1989)]. Specifically, the PCR reaction contains the following components: genomic DNA (0.5 µg), dNTPs (200 µM each), primers (30 picomoles each) and Taq polymerase (2.5 units). Typically, 30 cycles of PCR are performed, with each cycle comprising heating the sample to 95° for 1 minute, cooling to 54° for 15 seconds and then reheating to 73° for 3 minutes. In the last step of the final cycle the sample is heated to 73° for 10 minutes, instead of 3 minutes.

After the PCR reaction is complete, 1 unit of Klenow fragment is added to fill in any overhangs.

B. Fusion of a Known Stress Promoter DNA Fragment to the LacZ Gene in pRS415

The amplified DNA fragment containing the stress promoter is purified and then ligated into SmaI-cut pRS415 that has been treated with bacterial alkaline phosphatase. The ligation mixture is then used to transform lac⁻, Amp$^S$ *E. coli* cells by electroporation. Transformants are plated on LB+ampicillin (70 µg/ml)+X-gal (40 µg/ml). Colonies that are pale or dark blue are selected and replica plated onto two plates. One replica plate contains LB ampicillin (70 µg/ml)+X-gal (40 µg/ml). The other contains the same components plus a compound known to induce or repress the specific promoter. For stress-induced promoters, colonies that are darker blue on the compound-containing plate after overnight growth at 30° C. contain the desired promoter-lacZ fusion. For stress-repressed promoters, colonies that are lighter blue or white on the compound-containing plate contain the appropriate fusion.

EXAMPLE 3

Construction of *E. coli* Strain SF1

SF1 is a derivative of *E. coli* K12 strain GC4468. The parent strain has an F⁻, thi, rpsL, Δ(lac-pro) 169 genotype. Because of the thi mutation, the parent strain requires thiamine for growth. The preferred hosts of this invention should be wild-type for all genes, except lac. Therefore, I created SF1 by plating approximately $10^{10}$ GC4468 cells on plates containing M9+glucose medium. Colonies that grew on such medium must have reverted to a thi⁺ genotype. One such colony was selected and named SF1.

A sample of strain SF1 was deposited with the American Type Culture Collection ("ATCC"), 12301 Parklawn Drive, Rockville, Md. 20852 on Jun. 26, 1992 and given accession number 55337.

EXAMPLE 4

P1 Lysate Procedure for Moving Stress Promoter-LacZ Fusions between Host Strains This procedure allowed me to move a stress promoter-lacZ fusion from one host strain to another. In this manner, all stress promoter-lacZ fusions in a diagnostic kit can be put into the same host cell background. I used this technique to place all of the stress promoter-lacZ fusions into strain SF1.

P1 phage randomly nicks host cell DNA with its own endogenous endonuclease and packages the resulting DNA fragments into virions. Certain of the DNA fragments produced and packaged will contain the desired stress promoter-lacZ fusion.

The P1 lysate was made as follows. The cells containing the desired stress promoter-lacZ fusion, either on a plasmid or within the chromosome, were grown overnight in LB at 30° C. until early stationary phase. I then inoculated 50 µl of that culture into 5 ml LB containing 0.4% glucose and 5 mM CaCl$_2$ and incubated for 30 minutes at 30° C. I next added 0.1 ml of P1 phage (approx. $5 \times 10^8$ pfu/ml) to the culture and continued incubation for 2–4 hours, until cell lysis was apparent. I then added 0.1 ml of chloroform, vortexed for 10 seconds and centrifuged to remove cellular debris. The supernatant was stored at 4° C. with an additional 0.1 ml of chloroform.

I then performed transduction of the recipient strain, SF1. I grew SF1 in LB to early stationary phase. I then centrifuged the cells and resuspended them in 2.5 ml of 5 mM CaCl and 10 mM MgSO$_4$. I then mixed 0.1 ml of the cell suspension with either 10 µl or 100 µl of P1 lysate in separate tubes. I also had one tube with only 100 µl of cells and one tube with only 100 µl of P1 lysate as controls. I then incubated these tubes for exactly 20 minutes at 30° C., without shaking. I then added 0.1 ml of 1M Na citrate to each tube and centrifuged to pellet the cells. If the stress promoter is induced by a particular compound, the cells were resuspended in 50 µl of LB and plated onto LB+ampicillin (70 µg/ml)+X-gal (40 µg/ml)+the compound. Those colonies which were blue after overnight growth at 30° C. contained the stress promoter-lacZ fusion. If the stress promoter is repressed by a particular compound, the cells were resuspended in 50 µl of LB and plated onto LB+ampicillin (70 µg/ml)+X-gal (40 µg/ml). Blue colonies were selected and replica plated onto the same media or the same media plus the repressing compound. Colonies which were lighter blue or white on the compound-containing plate contained the desired fusion.

EXAMPLE 5

Toxin-Inducible β-Galactosidase Assays

I used two variations of the same assay to determine changes in stress promoter-linked β-galactosidase expression induced by various compounds.

The first assay was performed in small test tubes. *E. coli* host(s) harboring a stress promoter-lacZ gene fusion, were grown separately overnight with shaking in either LB supplemented with 70 µg/ml ampicillin or M9+G supplemented with 70 µg/ml ampicillin (180 ml H$_2$O, 20 ml 10X M9 salts (10X M9 salts=60 g Na$_2$HPO$_4$, 30 g KH$_2$PO$_4$, 5 g NaCl, 10 g NH$_4$Cl/liter), 2 ml 40% glucose, 0.4 ml 1M MgSO$_4$, 20 µl 1M CaCl$_2$) at 30° C. The next morning, one drop of each overnight culture was diluted into a series of tubes, each containing 1 ml of fresh media. This allowed me to test a range of concentrations of the compound on each host. The cells were then grown at 30° C. until they reached an optical density at 600 nm (OD$_{600}$) of 0.1–0.2.

At this point, one tube of each stress promoter-containing host was placed on ice and used to measure the OD$_{600}$ prior to the addition of the compound. The other tubes of each stress promoter-containing host were split into two, with one half receiving the compound to be tested (1 pM–1 mM, in 10-fold increments were routinely used) and the other half receiving no compound. The tubes which received no compound served as both a control for the effect of the compound on cell growth and as a baseline measurement of β-galactosidase expression.

The cultures were then incubated for an additional two hours at 30° C. A 0.5 ml aliquot of each culture was then removed for an OD$_{600}$ measurement. (If the OD$_{600}$ was too high to take an accurate reading, I diluted the 0.5 ml aliquot with an equal volume of fresh culture media, reread the sample at OD$_{600}$ and multiplied the reading times two.) I then took 200 µl from each culture and pipetted it into 800 µl of Z buffer (16.1 g Na$_2$HPO$_4$—7H$_2$O, 5.5 g NaH$_2$PO$_4$—H$_2$O, 0.75 g KCl, 0.246 g MgSO$_4$—7H$_2$O, 2.7 ml β-mercaptoethanol/liter, pH 7.0). To this I added 2 drops of toluene and vortexed the cultures for 10 seconds. I then added additional Z buffer to 2 ml final volume. The toluene/Z-buffered sample was then incubated in a 37° C. water bath for 40 minutes. The sample is then placed in a heating block, which had been pre-heated to 28° C., for 5 minutes. To start the colorimetric reaction, I added 200 µl of o-nitrophenyl galactose (ONPG; 4 mg/ml in Z buffer), while keeping exact record of the reaction time. When any particular sample tube turned light yellow, I added 0.5 ml of Na$_2$CO$_3$ to stop the reaction, as well as stopping the reaction in the corresponding control sample, noting the exact time elapsed from ONPG addition to Na$_2$CO$_3$ addition. The sample and the control were then read in a spectrophotometer at OD$_{420}$ and OD$_{550}$.

Units of activity were calculated using the following formula:

$$\text{Units activity} = 1{,}000 \times \frac{OD_{420} - (1.75)(OD_{550})}{\text{time} \times \text{culture volume} \times OD_{600}}$$

wherein time is the time elapsed from adding ONPG to stopping the reaction with Na$_2$CO$_3$, in minutes; culture volume is the volume used in the assay (in the above case, 0.2 ml); OD$_{420}$ and OD$_{550}$ are the differences in those OD values between the toxin samples and the control samples; and OD$_{600}$ is the reading obtained from the toxin-treated culture after incubation.

The second type of assay is performed in 96 well microtiter plates. In this assay, the appropriate *E. coli* hosts were grown separately overnight at 30° C. in either M9+G medium or LB medium. In either case, the medium was supplemented with 70 µg/ml ampicillin. The next day the cells were diluted 20-fold into fresh medium and grown at 30° C. until reaching an OD$_{600}$ of 0.2–0.4. I then pipetted 50 µl of each host cell into two rows of wells in a sterile 96-well microtiter plate. One row was used to measure the effect of the test compound on β-galactosidase expression. The other row was used to measure the effect of the test compound on cell growth.

I then made a 10-fold dilution series of the compound to be tested in culture medium, adding 50 µl of each dilution to the cells in wells 2 through 9 in each row of cells (i.e., well 2 received full-strength compound, well 3 received a 1:10 dilution of compound, well 4 received 1:100 dilution and so on). The cells in well 1 of each row received 50 µl of medium alone. An OD$_{600}$ measurement of all wells was then taken to account for any adsorbance that might be due to the test compound. The cells were then incubated for 90 minutes at 30° C. with moderate shaking. After incubation, an OD$_{600}$ measurement of all wells was taken and 1 drop of chloroform+10 µl of 1% SDS was added to each well in the first row. I then added 100 µl of Z buffer to each of the wells in the first row and incubated an additional 20 minutes at 30° C.

I then added 40 µl of ONPG (4 mg/ml in Z buffer) to each well in the first row, continued incubation at 30° C. and began timing the reaction. This allowed the cells in the second row to continue growth and thus ascertain the effect of the test compound on cell growth over a longer period of time. When a yellow color developed in any of the wells receiving ONPG, the reaction is stopped in all wells in the first row by the addition of 500 µl of 1M Na$_2$CO$_3$ and the time was carefully noted. The OD$_{420}$ and OD$_{550}$ of all wells in the first row was read and the units of activity measured by the formula set forth above. The cells in the second row were allowed to grow for an additional 90 minutes after the initial 90 minute incubation. An OD$_{600}$ measurement was taken every 30 minutes to monitor cell growth.

The same two assays were utilized when repression of stress promoter-controlled β-galactosidase expression was being assayed. The only difference was that yellow color developed in the control samples before the compound-containing samples. Once the yellow color developed in the control well, the reaction in both the control and compound-containing samples was stopped simultaneously.

Both the units of β-galactosidase activity and the culture $OD_{600}$ is plotted against the dose of compound for each dosage tested. Such plots allowed me to determine the $LD_{50}$ of a compound. These plots may also suggest that the test compound is toxic (via a decrease in $OD_{600}$ with increasing concentrations of compound), despite its failure to induce a particular promoter (no induction/suppression of β-galactosidase expression).

EXAMPLE 6

Construction of Specific Stress Promoter-lacZ Fusions

I. sodA

I obtained a sodA-lacZ fusion gene from Dr. Daniele Touati. He created the fusion using the phage Mu dX chromosomal random insertion technique described above in Example 1, part III. The transductants were screened for specific induction of β-galactosidase expression in the presence of paraquat. I moved the sodA-lacZ fusion into strain SF1 by P1-mediated transduction, as described in Example 3.

The sequence of sodA is known [D. Touati, *J. Bacteriol.*, 170, pp. 2511–20 (1988); and H. M. Hassan et al., *Proc. Natl. Acad. Sci. USA*, 89, pp. 3217–21 (1992), the disclosures of which are herein incorporated by reference]. Therefore, a sodA-lacZ fusion can be constructed using the PCR technique described in Example 2, part II and the following primers: 5'-ACGAAAAGTACGGCATTGAT-3' [SEQ ID NO:1] and 5'-GCTCATATTCATCTCCAGTA-3' [SEQ ID NO:2]. Transformants containing the desired fusion are identified by inducibility of β-galactosidase expression in the presence of either paraquat or metal chelators.

II. soi28

The soi28-lacZ fusion was constructed using the random Mu dX phage chromosomal insertion technique described above in Example 1, part III. The construction is described in T. Kogoma et al., *Proc. Natl. Acad. Sci. USA*, 85, pp. 4799–803 (1988), the disclosure of which is herein incorporated by reference. Transductants were screened for the ability to express β-galactosidase when induced by paraquat, as described in T. Kogoma et al., supra.

Alternatively, a soi28-lacZ fusion can be made using the PCR technique described in Example 2, part II and the following primers: 5'-GCTATGTGTGTGATGTGAGC-3' [SEQ ID NO:3] and 5'-TGATGACAGATGTCGCCCCA-3' [SEQ ID NO:4]. Desired fusions are detected by inducibility of β-galactosidase expression in the presence of paraquat.

III. katF

The katF gene is described by P. C. Loewen et al., *J. Bacteriol.*, 162, pp. 661–67 (1985), the disclosure of which is herein incorporated by reference. The katF gene encodes a hydrogen peroxide-inducible catalase activity. A katF-lacZ fusion was constructed by Mu dX insertion into a cloned katF gene on a plasmid, as described in Example 1, part II.

A katF-lacZ fusion is alternatively constructed using the PCR technique described in Example 2, part II and the primers: 5'-CAGGTGCGTTGTAGTGAGTT-3' [SEQ ID NO:5] and 5'-CAATAAACGAGATAACTCTCC-3' [SEQ ID NO:6]. The construct is tested for inducibility of β-galactosidase expression by phenolic acid or another weak organic acid.

IV. katG

The katG gene is described in P. C. Loewen et al., *J. Bacteriol.*, supra. A katG-lacZ fusion can be constructed using the PCR technique described in Example 2, part II and the following primers: 5'-AAGCTTAATTAAGATCAATTTG-3' [SEQ ID NO:7] and 5'-GCCGCAGAAAGCGGTTCGCC-3' [SEQ ID NO:8]. Transformants containing the desired fusion are identified by induction of β-galactosidase in the presence of $H_2O_2$.

V. ahp

The cloning and sequencing of the ahp gene was described by G. Storz et al., *J. Bacteriol.*, 171, pp. 2049–55 (1989); and by L. A. Tartaglia et al., *J. Mol. Biol.*, 210, pp. 709–19 (1989), the disclosures of which is herein incorporated by reference. An ahp-lacZ fusion can be constructed using the PCR technique described in Example 2, part II and the following primers: 5'-ATCGGGTTGTTAGTTAACGC-3' [SEQ ID NO:9] and 5'-CTATACTTCCTCCGTGTTTTCG-3' [SEQ ID NO:10]. Desired fusions are detected by inducibility of β-galactosidase expression in the presence of cumene hydroperoxide or tert-butyl hydroperoxide.

When an ahp-lacZ fusion is employed in the methods and kits of this invention, the construct should be present in both a wild type *E. coli* and a mutant strain of *E. coli* which cannot synthesize or degrade fatty acids (fabB, fadE strain). The mutant strain provides the ability to identify a compound that causes lipid peroxidation. Peroxidation-sensitive, mammalian cell-specific fatty acids, such as linolenic acid and linoleic acid, can be inserted into the bacterial membrane of such a strain by growing it in media containing those fatty acids. When a transformant of the mutant strain is induced to express β-galactosidase by a compound, but a wild-type transformant is not, the compound in question must cause lipid peroxidation.

Moving the ahp-lacZ fusion construct from the original strain to another stain is achieved via the P1 lysate procedure described in Example 3.

VI. nfo

The nfo gene encodes a DNA repair enzyme that is specific for oxidative damage that shatters the imidazole ring of nucleic acids. It is induced by redox active agents, such as those that cause superoxide radical formation. The nfo gene was described by R. Cunningham et al., *Proc. Natl. Acad. Sci. USA*, 82, pp. 474–78 (1985), the disclosure of which is herein incorporated by reference. The nfo-lacZ construct was created as described in S. Saporito et al., *J. Bacteriol.*, 170, pp. 5141–45 (1988), the disclosure of which is herein incorporated by reference. I obtained this construct from Dr. Richard Cunningham.

An nfo-lacZ fusion can be constructed using the PCR technique described in Example 2, part II and the following primers: 5'-CATCGCATAAACCACTACAT-3' [SEQ ID NO:11] and 5'-GTTACTGCCCTGACCGGCGG-3' [SEQ ID NO:12]. Fusions are screened for inducibility of β-galactosidase expression in the presence of paraquat.

VII. sdh

Expression of the sdh gene is inhibited by lack of oxygen or inhibition of electron transport. Thus, detection of sdh induction is indicated by a decrease in assayable product expression.

The sdh-lacZ fusion was made by Mu dX insertion into the sdh gene contained on a plasmid provided by Dr. John Guest, University of Sheffield, England, as described in Example 1, part II. Transformants were assayed by incubation under anaerobic conditions.

The sequence of sdh has been published [S.S. Ner et al., *Biochemistry*, 22, pp. 5243–48 (1983), the disclosure of which is herein incorporated by reference]. An sdh-lacZ fusion can be constructed using the PCR technique described in Example 2, part II and the following primers: 5'-GAATTCGACCGCCATTGCGC-3' [SEQ ID NO:13] and 5'-AAGTCGGTATTTCACCTAAG-3' [SEQ ID NO:14]. Transformants are assayed for the presence of the fusion by depressed β-galactosidase expression under anaerobic conditions.

VIII. dinD

I obtained this construct from Graham Walker who made this fusion as described in S. Kenyon et al., *Nature*, 289, pp. 808–12 (1981), the disclosure of which is herein incorporated by reference. This construct was made by the same Mu dX insertion procedure described in Example 1, part III. Transductants containing the fusion were identified by expression of β-galactosidase in the presence of mitomycin C.

I moved the dinD-lacZ fusion into strain SF1 by the P1 transduction technique described in Example 3. The resulting strain containing the dinD-lacZ fusion is named SF923.

A sample of SF923 was deposited with the American Type Culture Collection, 12301 Parklawn Drive, Rockville, Md. 208520 on Jun. 26, 1992 and has been given accession number 55336.

IX. rpoD

I obtained an rpoD-lacZ fusion from another source who created it using the Mu dX chromosomal insertion technique described in Example 1, part III. I moved the rpoD-lacZ fusion into *E. coli* strain SF1 by P1 transduction as described in Example 3.

Alternatively, an rpoD-lacZ fusion can be constructed using the PCR technique described in Example 2, part II and the following primers: 5'-AAGCTTGCATTGAACTTGTG-3' [SEQ ID NO:15] and 5'-GTTTGCCGCCTGCTCTTCCC-3' [SEQ ID NO:16]. Desired fusions are detected by β-galactosidase expression in the presence of ethanol.

X. hag

The hag-lacZ fusion was constructed by a Mu dX into a plasmid containing a cloned hag gene, as described in Example 1, part II. Transformants were screened for repression of β-galactosidase expression in the presence of CCCP.

The sequence of the hag gene is known [G. Kuwajima et al., *J. Bacteriol.*, 168, pp. 1479–83 (1987), the disclosure of which is herein incorporated by reference]. Thus, a hag-lacZ fusion may be constructed using the PCR technique described in Example 2, part II and the following primers: 5'-GACGGCGATTGAGCCGACGG-3' [SEQ ID NO:17] and 5'-TTAGTACCGGTAGTGGCCTG-3' [SEQ ID NO:18]. Transformants are tested for the presence of the desired fusion by decreased expression of β-galactosidase in the presence of compounds that disrupt membrane integrity, such as CCCP.

XI. ada

We constructed an ada-lacZ fusion using the Mu dX insertion technique described in Example 1, part II, into a plasmid containing the ada gene. That plasmid was obtained from Dr. Leona Samson at Harvard University. Transfectants were selected on the basis of induction of β-galactosidase expression in the presence of MMS.

The nucleotide sequence of the ada gene has been published [Y. Nakabeppu et al., *J. Biol. Chem.*, 260, pp. 7281–88 (1985), the disclosure of which is herein incorporated by reference]. Therefore, an ada-lacZ construct can be created by employing the PCR technique described in Example 2, part II and the following primers: 5'-AAGCTTCCTTGT-CAGCGAAA-3' [SEQ ID NO:19] and 5'-CAGCGTTTCGTCAGCTTTGC-3' [SEQ ID NO:20]. Transformants are tested for the presence of the desired fusion by inducibility of β-galactosidase expression in the presence of MMS.

XII. gyr

A gyr-lacZ fusion was constructed using the Mu dX insertion method into a plasmid containing the gyr gene as described in Example 1, part II. The resulting transfectants are screened for induction of β-galactosidase expression in the presence of nalidixic acid.

The sequence of the gyrA gene was described by H. Yoshida et al., *Mol. Gen. Genet.*, 211, pp. 1–7 (1988), the disclosure of which is herein incorporated by reference. A gyr-lacZ fusion can be constructed using the PCR technique described in Example 2, part II and the following primers: 5'-CTACGTTATGGTTTACCGGC-3' [SEQ ID NO:21] and 5'-AAGTACGCGACGGTGTACCG-3' [SEQ ID NO:22]. Transformants containing the desired fusion are identified by inducibility of β-galactosidase expression in the presence of nalidixic acid.

XIII. top

I used the Mu dX chromosomal insertion technique described in Example 1, part III, to create a library from which to select top-lacZ fusions. The library is screened for induction of β-galactosidase expression in the presence of acridine orange to isolate clones containing the desired fusion.

The top gene was sequenced by T.-D. Dinh et al., *J. Mol. Biol.*, 191, pp. 321–31 (1986), the disclosure of which is herein incorporated by reference. A top-lacZ fusion is alternatively constructed using the PCR technique described in Example 2, part II and the following primers: 5'-GCAT-CAACCGCAGGTTGCGC-3' [SEQ ID NO:23] and 5'-CACCGGCGTCACGCAGCGTA-3' [SEQ ID NO:24]. Transformants containing the desired fusion are identified by inducibility of β-galactosidase expression in the presence of a DNA intercalating agent, such as acridine orange or ethidium bromide.

XIV. clpB

I constructed a clpB-lacZ fusion from a plasmid containing the clpB gene using the Mu dX insertion method described in Example 1, part II. Transductants were screened for induction of β-galactosidase expression in the presence of puromycin, a compound known to produce truncated proteins.

The clpB gene has recently been sequenced [C. L. Squires et al., *J. Bacteriol.*, 173, pp. 4254–62 (1991), the disclosure of which is herein incorporated by reference]. Alternatively, a clpB-lacZ fusion can be constructed using the PCR technique described in Example 2, part II and the following primers: 5'-GATCCGGTACGCGTGATTT-3' [SEQ ID NO:25] and 5'-CCAGACGCATAACTCCTCCC-3' [SEQ ID NO:26]. Those transformants that can be induced to express β-galactosidase upon exposure to canavanine, puromycin or heat contain a clpB-lacZ fusion.

XV. merR

The merR gene is described by W. Ross et al., *J. Bacteriol.*, 171, pp. 4009–18 (1989), the disclosure of which is herein incorporated by reference. I obtained the merR-lacZ fusion from Dr. Ann Summers, in Dr. Ross' laboratory.

A merR-lacZ fusion is alternatively constructed using the PCR technique described in Example 2, part II and the following primers: 5'-CGCTTGACTCCGTACATGAG-3' [SEQ ID NO:27] and 5'-TGGATAGCGTAACCTTACTT-3' [SEQ ID NO:28]. Those transformants that express β-galactosidase upon exposure to methyl mercury contain the desired fusion.

XVI. fepB-entC

I constructed a fepB-entC-lacZ fusion by Mu dX insertion into a plasmid-encoded fepB-entC gene. I measured induction by treating the resulting transformants with the metal chelator, EGTA.

Alternatively, a fepB-entC-lacZ fusion can be constructed using the PCR technique described in Example 2, part II and the following primers: 5'-CCACAAGATGCAAC-CCCGAG-3' [SEQ ID NO:29] and 5'-GACGTATCCATAT-CATCCTCC-3' [SEQ ID NO:30], based on the reported nucleotide sequence of the fepB gene [M. F. Elkins et al., *J. Bacteriol.*, 171, pp. 5443–51 (1989)]. Transformants are screened for the presence of the desired fusion as described in T. J. Brickman et al., *J. Mol. Biol.*, 212, pp. 669–82 (1990), the disclosure of which is herein incorporated by reference.

XVII. cyo

I received a cyo-lacZ fusion from Dr. C. C. Lin in Dr. Iuchi's laboratory at Harvard Medical School.

A partial sequence of the cyo operon was published by J. Minagawa et al., *J. Biol. Chem.*, 265, pp. 11198–203 (1990), the disclosure of which is herein incorporated by reference. An cyo-lacZ fusion can be constructed using the PCR technique described in Example 2, part II and the following primers: 5'-TTGACGATGGACGCGCTGGA-3' [SEQ ID NO:31] and 5'-CAATTGGTATAACCAATGTG-3' [SEQ ID NO:32]. The resulting lacZ fusion is identified by incubating the transformants under anaerobic conditions and selecting those transformants that exhibit repressed β-galactosidase expression.

XVIII. gsh

I constructed a gsh-lacZ fusion by Mu dX insertion into a plasmid carrying the gsh gene. This technique is described in Example 1, part II. I selected for clones which expressed β-galactosidase in the presence of NEM.

The gsh gene has been cloned and sequenced [H. Gushima et al., *Nucleic Acids Res.*, 12, pp. 9299–307 (1985), the disclosure of which is herein incorporated by reference].

Therefore, a gsh-lacZ fusion can be made using the PCR technique described in Example 2, part II and the following primers: 5'-AAGCTTCAGCAGTGGCAGAA-3' [SEQ ID NO:33] and 5'-GTATAAACCGCCTTCCGGGCC-3' [SEQ ID NO:34]. Transformants are screened with N-ethylmaleimide.

XIX. mutT

A mutT-lacZ fusion was created using the Mu dX insertion technique into a plasmid-encoded version of the mutT gene as described in Example 1, part II. Transformants are screened for β-galactosidase expression after exposure to X-ray irradiation.

The sequence of the mutT gene was published by M. Akiyama et al., *Mol. Gen. Genet.*, 206, pp. 9–16 (1987), the disclosure of which is herein incorporated by reference. Thus, a mutT-lacZ fusion is alternatively constructed using the PCR technique described in Example 2, part II and the following primers: 5'-CTGCACTGGCGGCGCAAACC-3' [SEQ ID NO:35] and 5'-ATAAGACGCGGACAGCGTCG-3' [SEQ ID NO:36]. Transformants containing the desired construct are screened for β-galactosidase expression after exposure to X-ray irradiation.

XX. unc

I constructed an unc-lac fusion by Mu dX insertion into a plasmid containing a cloned unc gene. Transformants were screened for β-galactosidase expression in the presence of 2,4-dinitrophenol.

A partial sequence of the unc operon was published by H. Kanazawa et al., *Biochem. Biophys. Res. Commun.*, 103, pp. 604–12 (1981), the disclosure of which is herein incorporated by reference. Thus, an unc-lacZ fusion can be constructed using the PCR technique described in Example 2, part II and the following primers: 5'-AAAGCAAATAAATT-TAATTTTT-3' [SEQ ID NO:37] and 5'-GGCCACCCGGC-CTTTCGCTG-3' [SEQ ID NO:38]. Transformants are screened for inducibility of β-galactosidase expression in the presence of 2,4-dinitrophenol.

XXI. rdc

I obtained a strain containing an rdc-lacZ fusion from Dr. G. T. Javor. The fusion was made using the random Mu dX insertion technique described in Example 1, part IIIA. Transfectants were screened for the presence of the fusion by incubating on X-gal plates in the presence of thioglycerol. Colonies which were blue in such an assay contained the desired fusion.

The rdc-lacZ fusion was transferred from the source strain to SF1 using the P1 transduction technique described in Example 4. A strain containing this fusion was named SF924.

A sample of SF924 was deposited with the American Type Culture Collection, 12301 Parklawn Avenue, Rockville, Md., 20852 on Jun. 26, 1992 and was assigned accession number 55335.

XXII. lon

The sequence of the lon gene and the location of the promoter has been described by T. A. Phillips et al., *J. Bacteriol.*, 159, pp. 283–87 (1984), the disclosure of which is herein incorporated by reference. A lon-lacZ fusion is constructed using the PCR technique described in Example 2, part II and the following primers: 5'-TCTCGGCGT- TGAATGTGGG-3' [SEQ ID NO:39] and 5'-CGACGTCT-TCCATGGACGGC-3' [SEQ ID NO:40]. Transformants are screened for inducibility of β-galactosidase expression in the presence of puromycin.

XXIII. leu-500

The sequence of the leu-500 gene, which contains a single point mutation in the promoter, has been described by R. M. Gemmill et al., *J. Bacteriol.*, 158, pp. 948–53 (1984), the disclosure of which is herein incorporated by reference. A leu-500-lacZ fusion is constructed using the PCR technique described in Example 2, part II and the following primers: 5'-GTCAACAAAATGCAATGGCG-3' [SEQ ID NO:41] and 5'-GCGTTATGCTTTTAGTGGCACTGG-3' [SEQ ID NO:42]. Transformants are screened for inducibility of β-galactosidase expression in the presence of nalidixic acid or coumermycin.

XXIV. meto

The sequence of the meto gene has recently be been reported by M. Rahman et al., *GenBank/EMBL Database*, accession #M89992, the disclosure of which is herein incorporated by reference. A meto-lacZ fusion is constructed using the PCR technique described in Example 2, part II and the following primers: 5'-AAGCTTACACAGCATAACTG-3' [SEQ ID NO:43] and 5'-CCAGGCAGGGCATCG-GCGGGGG-3' [SEQ ID NO:44]. Transformants are screened for inducibility of β-galactosidase expression in the presence of N-ethylmaleimide.

EXAMPLE 7

Assay of Known Carcinogens Using Various Stress Promoters

We assayed a number of different chemicals for their ability to induce the expression of various stress promoter-lacZ fusions described above. The chemicals used for these assays were methyl mercury (0–1 µM), 4-nitroquinoline oxide ("4-NQO") (0–100 picomolar), MMS (0–40 nM), paraquat (0–50 µM), plumbagin (0–160 µM), mitomycin (5 µg/ml), 2,2'-dipyridyl (0–160 µM), $H_2O_2$ (0–1600 µM) and NaCl for osmotic stress (0–0.8M). We also subjected certain stress promoter-lacZ fusions to variations in pH and growth temperature.

These results provide important insight into the types of compounds that induce various stress promoters. For example, FIG. 1 demonstrates that mercury specifically induces the merR promoter, but not the sfiA or sodA promoter. Thus, it can be concluded that mercury has no effect on DNA replication (a stress that induces the sfiA promoter) and does not cause the formation of superoxides (a stress that induces sodA).

Figure 2:
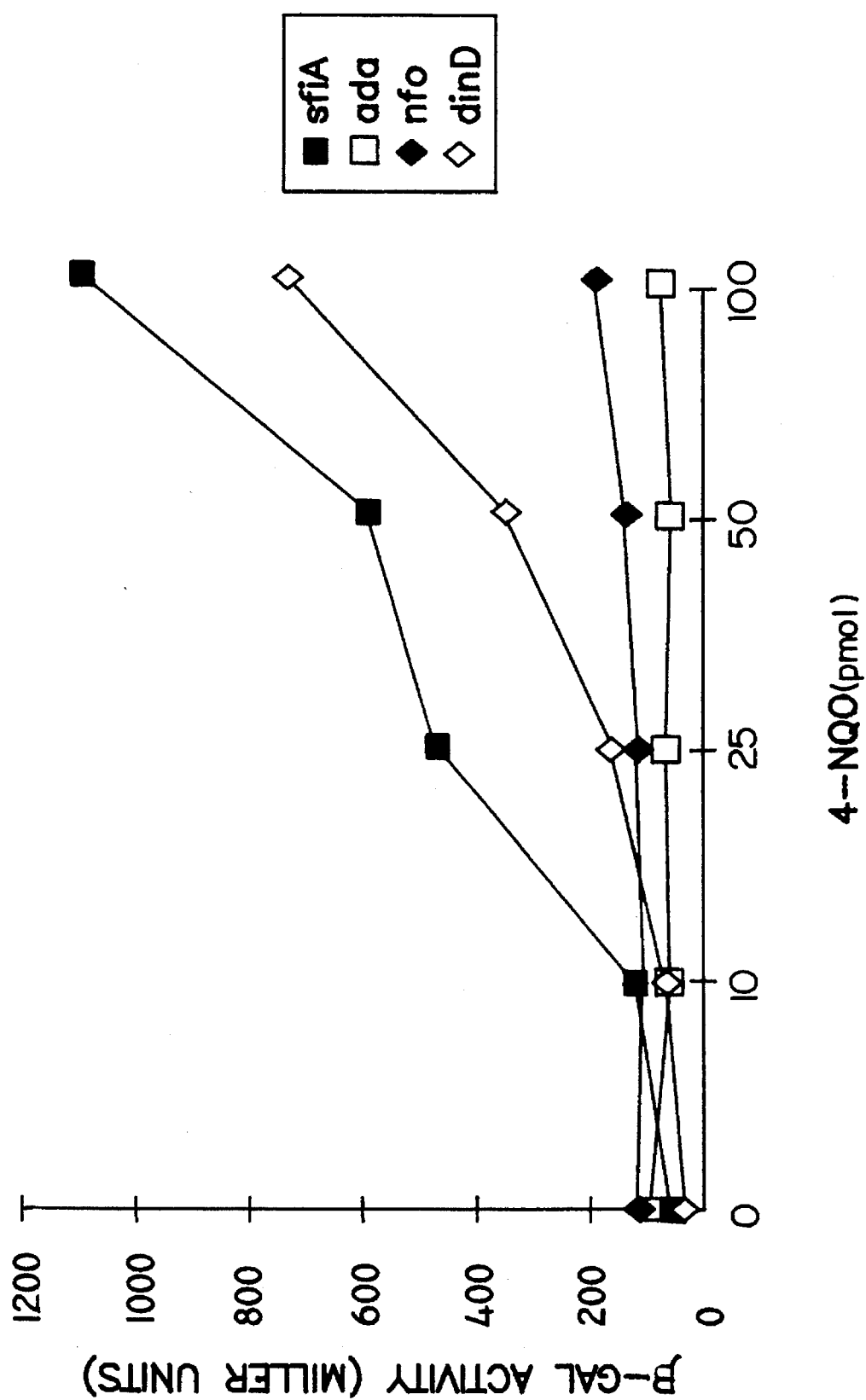
FIG. 2 depicts the induction of the sfiA, ada-alkA, nfo and dinD promoters by varying concentrations of 4-nitroquinoline, as measured by β-galactosidase synthesis.

FIG. 2 demonstrates that 4-NQO causes DNA replication damage (induction of the sfiA and dinD promoters), specifically via DNA strand breaks (dinD promoter), not DNA alkylation (adaA promoter). The minor, but dose-dependent induction of the nfo promoter suggests that the DNA damage caused by 4-NQO is oxygen-dependent.

Figure 3:
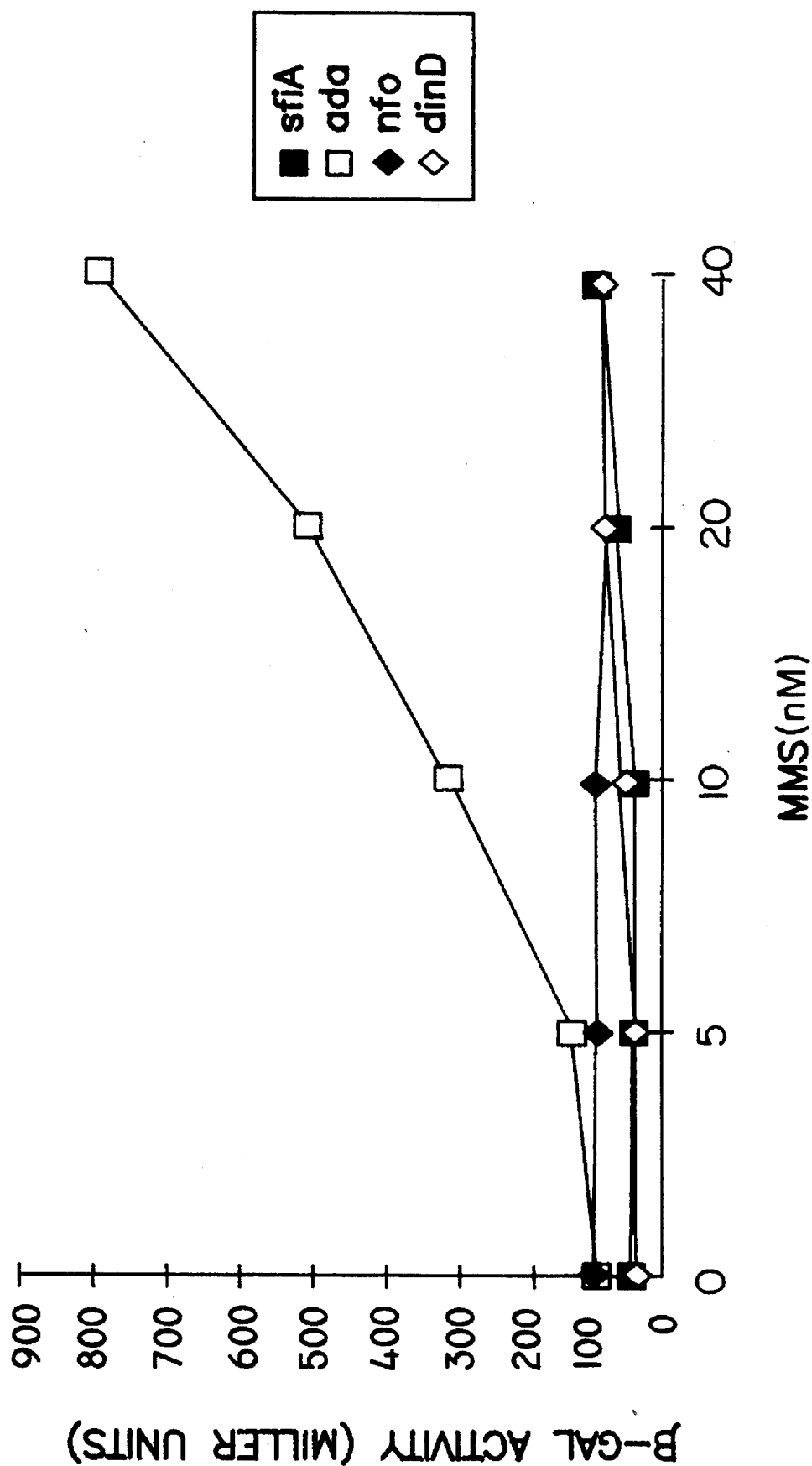
FIG. 3 depicts the induction of the sfiA, ada-alkA, nfo and dinD promoters by varying concentrations of methyl methanosulfate, as measured by β-galactosidase synthesis.

MMS apparently causes DNA damage by alkylating DNA (induction of the adaA promoter), not via stand breaks (dinD promoter). The alkylation caused by MMS is not oxygen-dependent (nfo promoter). These results are depicted in FIG. 3.

Figure 4:
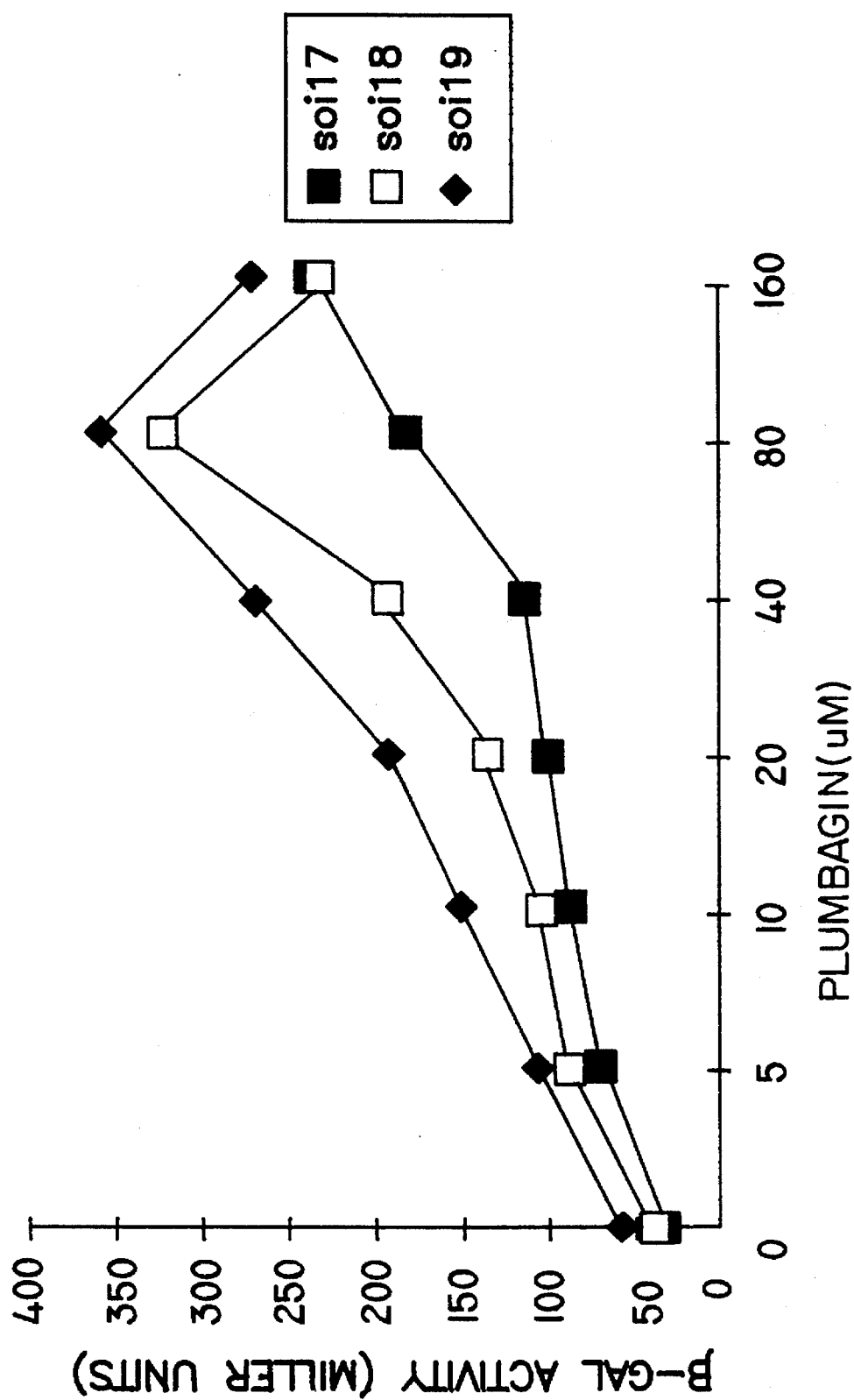
FIG. 4 depicts the induction of the soi17, soi19 and soi28 promoters by varying concentrations of plumbagin, as measured by β-galactosidase synthesis.

Both paraquat (see Table below) and plumbagin (see FIG. 4) cause induction of the soi28 promoter. In addition, paraquat also induced the nfo promoter, indicating that the compound causes oxygen-dependent DNA damage. Paraquat had a negligible effect in inducing the anaerobiosis- and transition metal-sensitive ndh promoter. The results with both paraquat and plumbagin are particularly relevant because neither compound produces a positive response in the widely employed Ames Assay.

TABLE 1

Induction of Stress Promoter-Controlled β-Galactosidase Expression By Paraquat

| Paraquat (µM) | ndh* | soi28 | nfo |
|---|---|---|---|
| 0 | 464 | 670 | 2952 |
| 50 | 980 | 2370 | 8100 |

*Induction of the various promoters is measured by β-galactosidase activity and expressed in units, as described in Example 5.

For the mitomycin assay, I only employed one concentration of the compound, but varied the time of exposure from 0–55 minutes. The results, depicted in the table below, demonstrate that after 55 minutes of exposure to mitomycin, the dinD promoter is induced by approximately 4-fold. This indicated that mitomycin caused DNA strand breaks.

TABLE 2

Effect Of Mitomycin C on dinD Controlled β-Galactosidase Expression

| Time of Exposure (Min) | dinD |
|---|---|
| 0 | 321 |
| 15 | 350 |
| 25 | 1036 |
| 35 | 811 |
| 55 | 1204 |

Figure 5:
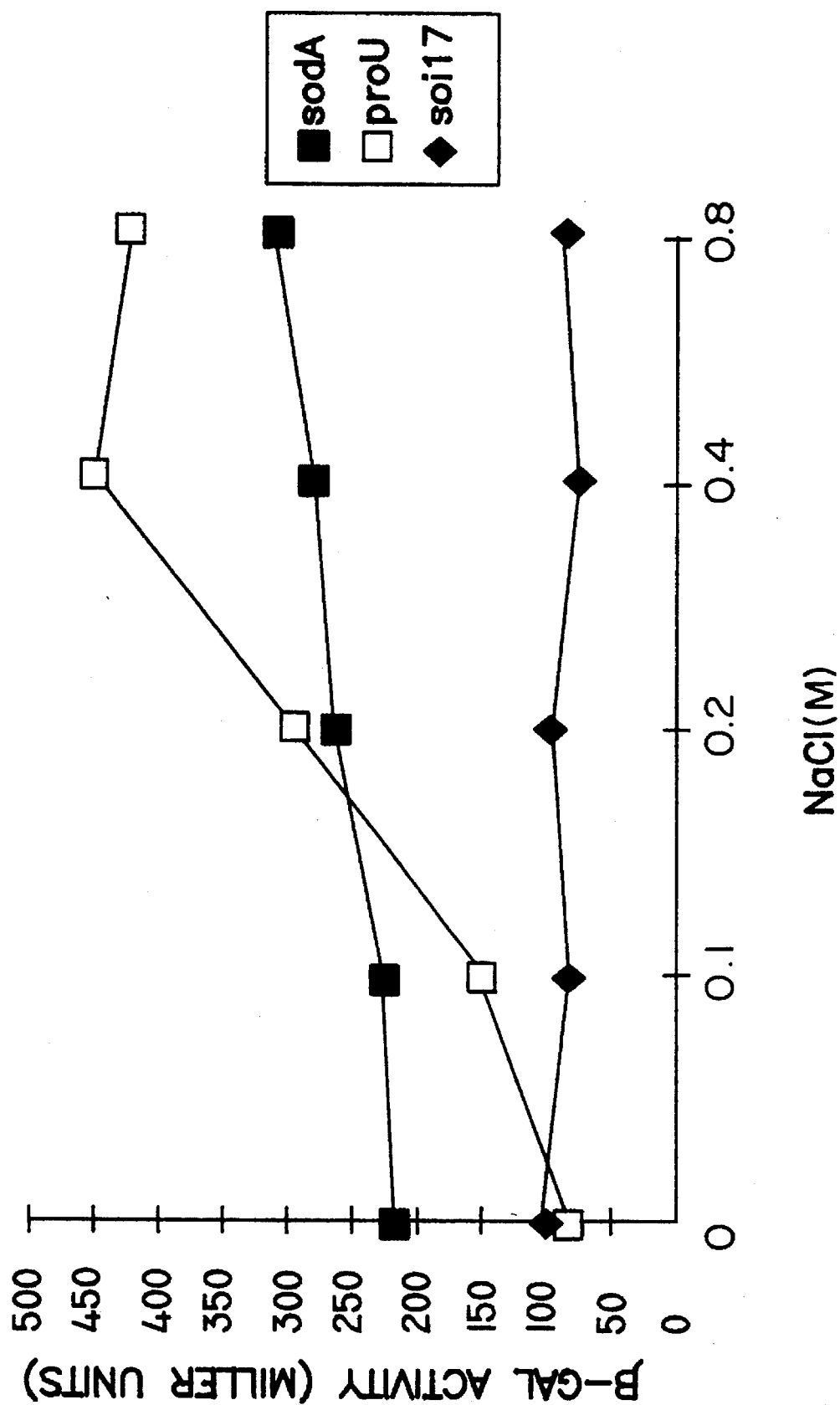
FIG. 5 depicts the induction of the sodA, proU and soi17 promoters by varying concentrations of sodium chloride, as measured by β-galactosidase synthesis.
Figure 6:
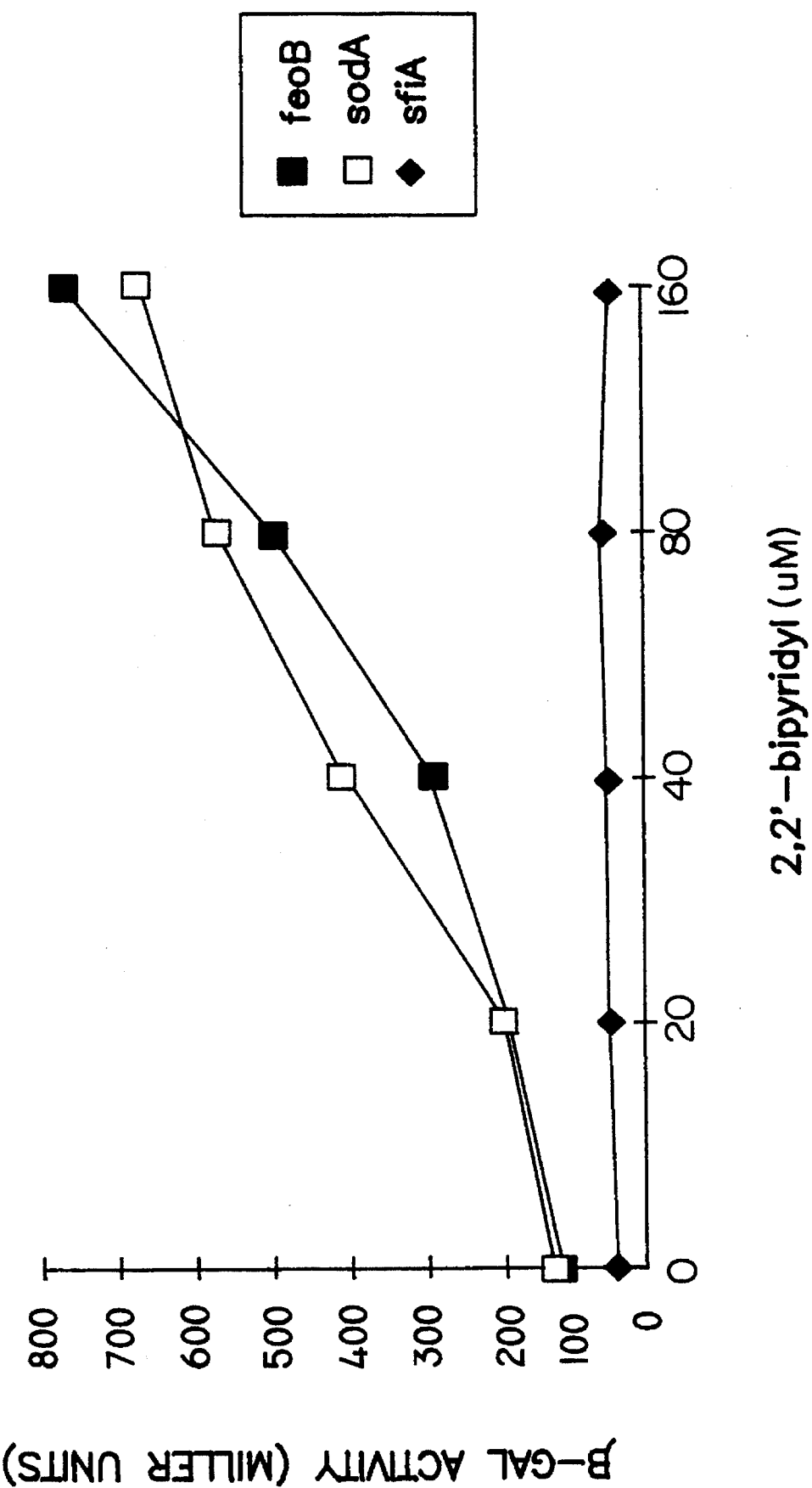
FIG. 6 depicts the induction of the fepB, sodA and sfiA promoters by varying concentrations of 2,2'-dipyridyl, as measured by β-galactosidase synthesis.

As expected, increased osmotic pressure (increased NaCl concentration) induces the proU promoter, but does not result in superoxide formation (no induction of sodA or soi17) (FIG. 5). In contrast, 2,2'-dipyridyl causes superoxide formation (sodA induction), as well as chelating metals (fepB induction). 2,2'-dipyridyl has no effect on DNA replication (sfiA promoter). This is depicted in FIG. 6.

To see how hosts harboring the rpoD promoter responded to heat shock, I incubated those hosts at 43° C. instead of 30° C. for 0–50 minutes. The results of this assay, depicted below, demonstrate a 3-fold induction of the rpoD promoter after 20 minutes. The decrease in induction observed after 30 and 50 minutes was attributed to increased cell death, not a reversal of induction.

TABLE 3

Effect of Increased Culture Temperature On rpoD Promoter Controlled Expression Of β-Galactosidase

| Time of Exposure (min) | rpoD |
|---|---|
| 0 | 1923 |
| 2 | 3362 |
| 5 | 3798 |
| 10 | 4471 |
| 20 | 6107 |
| 30 | 5561 |

Figure 7:
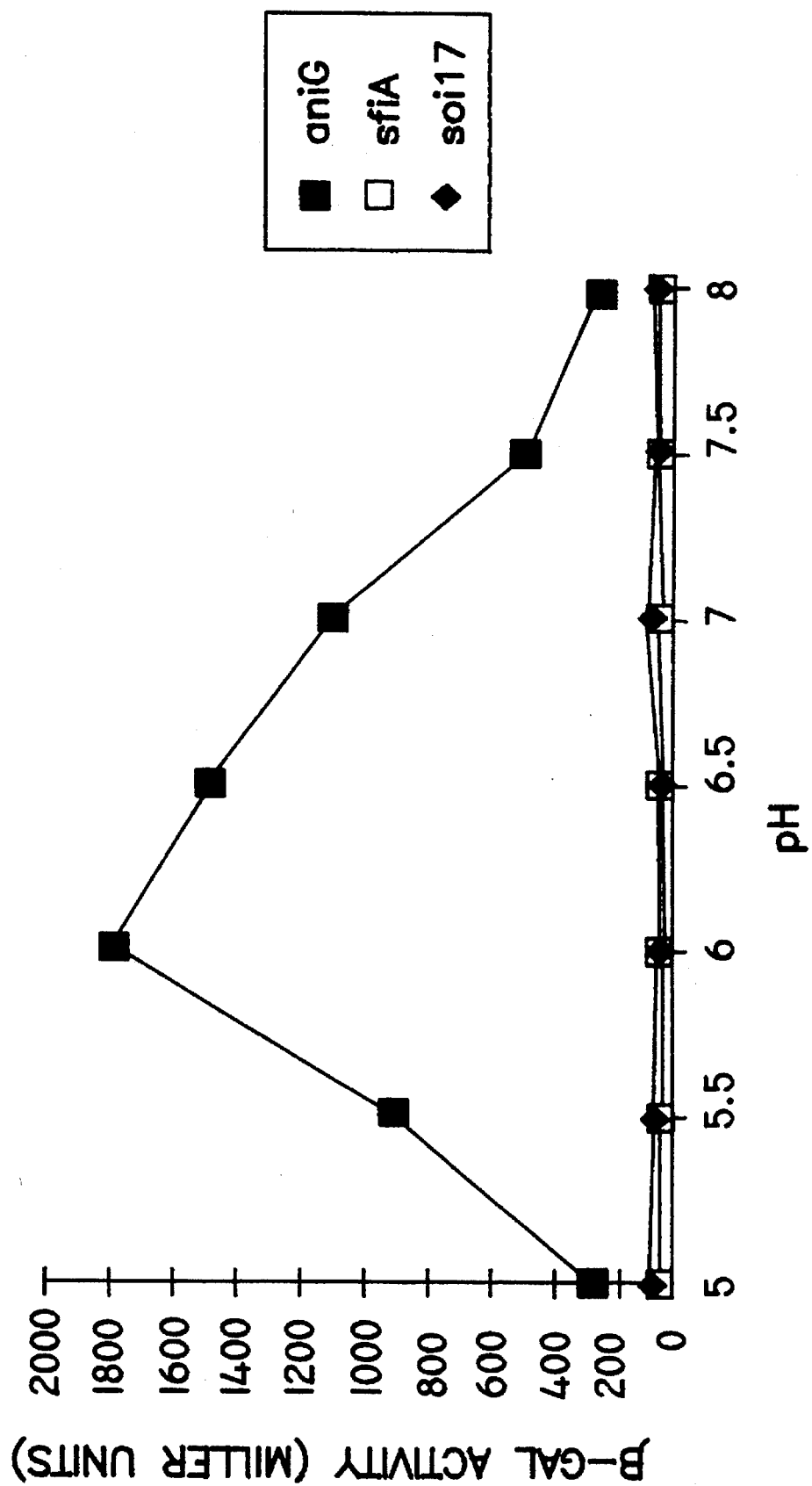
FIG. 7 depicts the induction of the aniG, sfiA and soi17 promoters at various pH, as measured by β-galactosidase synthesis.
Figure 8:
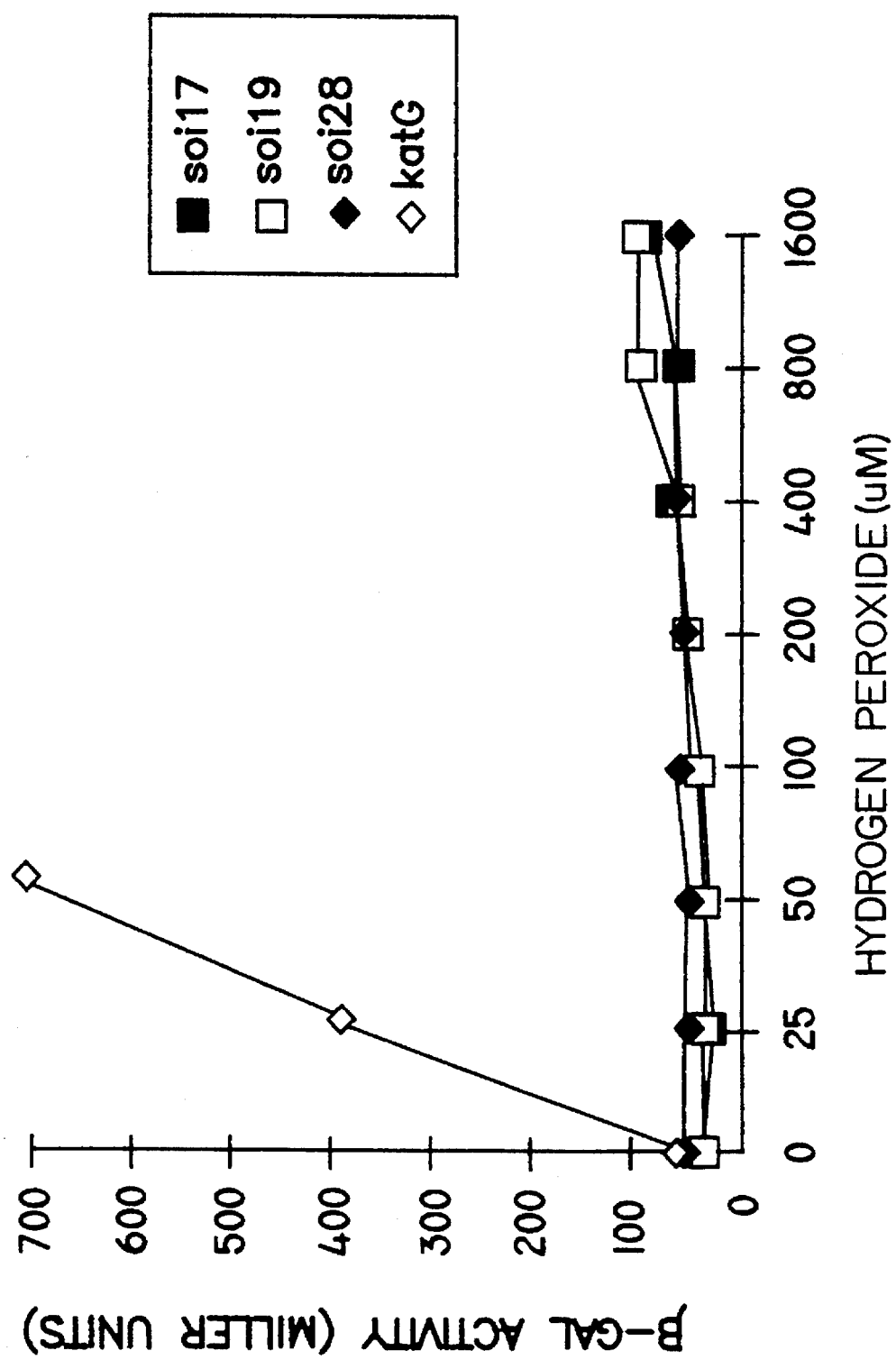
FIG. 8 depicts the induction of the soi17, soi19, soi28 and katG promoters by varying concentrations of hydrogen peroxide, as measured by β-galactosidase synthesis.

Finally, I assayed the effect of incubating hosts harboring different stress promoter-lacZ fusions in media having pH ranging from 5–8. The results, which are depicted in FIG. 7, demonstrate that the sfiA and soi17 promoters were not induced at any of the different pH. The aniG promoter showed maximal induction at pH 6.0 and a linear decrease in induction at both higher and lower pH.

EXAMPLE 8

Identification of Antitoxins

After an unknown compound is found to be a toxin on the basis of its induction or suppression of stress promoter controlled β-galactosidase expression, the same process can be utilized to identify a potential antitoxin.

An unknown compound is demonstrated to induce expression of β-galactosidase in both a host harboring a dinD-lacZ construct and a host harboring a katG-lacZ construct. This indicates that the compound is causing the production of hydrogen peroxide (katG induction) in sufficiently high concentrations to cause DNA strand breaks (dinD induction). Ascorbic acid is known to reduce the number of hydrogen peroxide induced DNA strand breaks, and therefore is a potential antitoxin to this unknown compound.

Hosts containing the katG-lacZ and hosts containing the dinD-lacZ are each plated into 8 wells in a 96 well microtiter dish. Each well is incubated with a different dilution of ascorbic acid for 30 minutes at 30° C. The first well is a control and receives no ascorbic acid. Each well is then exposed to the concentration of unknown compound previously determined to be optimum for maximum β-galactosidase induction. The assay is then carried out as described in Example 5. If the hosts in the ascorbic acid-treated wells express lower levels of β-galactosidase than in the control well, it is considered to be an antitoxin.

EXAMPLE 9

Improved Toxin-Inducible β-Galactosidase Assay

Two 96 well microtiter plates were used for each compound to be assayed. One plate contained strains harboring fusions to "strong" promoters: gyrA, katG, micF, topA, ada, cyd ($amp^R$), hag ($amp^R$) and zwf ($amp^R$). The other plate contained strains harboring fusions to "weak" promoters (any drug resistance of the strain is indicated in parentheses): groE, clpB, katF, merR, soi28 ($amp^R$), dinD ($amp^R$), aniG ($kan^R$) and nfo ($kan^R$).

Cultures of each of the above strains were grown separately in 1 ml LB broth containing the appropriate antibiotic if necessary (100 μg ampicillin or 50 μg kanamycin) overnight at 37° C. with good aeration. I then placed 250 μl of a 1:117 dilution of each culture in wells 2–11 of separate rows. Well 1 of each row contained 225 μl of LB+antibiotic. Well 12 of each row contained 25 μl of the undiluted overnight culture and 300 μl of LB+antibiotic. I then incubated the plates at 37° C. for 2 hours with good aeration. After 2 hours, I measured and recorded the $OD_{600}$ of the cultures.

The chemical to be tested was dissolved in a minimal volume of solvent (preferably water). Each chemical was tested over a range of 5-fold dilutions. I added 25 μl of the appropriate dilution to a given well in each row (i.e., well 2 in each row received 25 μl of undiluted chemical, well 3 in each row received 25 μl of a 1:5 dilution, well 4 in each row received 25 μl of a 1:25 dilution, and so on). Well 1 in each row received 25 μl of sterile water. After adding the chemical to be tested I measured the $OD_{600}$ of the wells again. I then incubated the plates for 37° C. for 2 hours with good aeration.

Following incubation with the chemical, I measured and recorded the $OD_{600}$ of each well. This $OD_{600}$ reading was used when calculating β-galactosidase activity. I then pipetted 200 μl of the cells from each well into a corresponding well of a chloroform-resistant polypropylene 96 well microtiter plate. I then added 50 μl of chloroform to each well in a fume hood and mixed by pipetting up and down. The plates were then left at room temperature for 15 minutes to allow the cells to permeabilize. Well 1 received 210 μl of Z buffer and 40 μl of ONPG solution.

While the cells were permeabilizing I put 170 μl of Z buffer and 40 μl of ONPG (4 mg/ml in Z buffer) into each of wells 2–13 of two 96 well microtiter plates ("reaction plates"). I then pipetted 40 μl of the permeabilized cells (taking care not to remove any chloroform) from each well into the corresponding well in the reaction plates and mixed by pipetting up and down. When all the wells were filled, the plate was placed into a Ceres 900 microplate reader (Biotek, Burlington, Vt.) and analyzed by measuring the $OD_{420}$ every minute for 30 minutes. Well 1 in each row served as the blank. At the end of 30 minutes, the $OD_{550}$ of each well was recorded for use in activity calculation. The $OD_{420}$ versus time for each well was then plotted and the slope of the linear portion of the resulting curve was calculated. The β-galactosidase activity was calculated by the following formula:

$$\frac{[t_x - t_o] \times (\text{slope}) + C_1 - OD_{550}}{(t_x) \times (OD_{600}) \times (\text{vol})}$$

where $t_o$ was the lag time between the addition of the cells to the ONPG and the time at which the plate was placed into the plate reader; $t_x$ was the total time between the addition of the cells to the ONPG and the end of the minute read; $C_1$ was the initial $OD_{420}$ reading from the plate reader; and "vol" was the volume of cells (40 μl) divided by the total volume in the reaction well (210 μl). The activity was then compared to the β-galactosidase activity of each strain incubated in the absence of chemical to give a "fold induction" value.

The results were then plotted on a three-dimensional histogram which showed the fold induction for each stress promoter at each concentration of chemical. Examples of such histograms are shown in FIGS. 9–12.

EXAMPLE 10

Construction of Additional Stress Promoter-lacZ Fusions

XXV. micF

I constructed a micF-lacZ fusion using the PCR technique described in Example 2, part II and the following primers: 5'-ATATGAATTCGTCGGCAAGTCCATTCTCC CC-3' [SEQ ID NO:45]; and 5'-ATATGGATCCGCGGGAGTTAT TCTAGTTGCC-3' [SEQ ID NO:46].

Transformants were screened for inducibility of β-galactosidase expression in the presence of ethanol.

XXVI. ada

I constructed an improved ada-lacZ fusion as follows. I synthesized the following two oligonucleotides which represented portions of the top and bottom strand of the ada promoter: 5'-TATAGAATTCC CTTGTCAGC-GAAAAAAATTAAAGCGCAAGATTGTTG-GTTTTTGCGTGATGGTGAC CGGGCAGCCTAAAG-GCTATCC-3' [SEQ ID NO:47]; and 5'-ATATG GATCCAATCAGCTCCCTGGTTAAGGAT-AGCCTTTAGGCTGCCCGGTCACCATCAC GC-3' [SEQ ID NO:48].

The two oligonucleotides had 30 base pairs of homologous overlap. I annealed the oligonucleotides and then incubated with Klenow fragment to complete synthesis of the double stranded promoter. I then digested the double stranded promoter with EcoRI and BamHI. The digested promoter was then cloned into EcoRI/BamHI digested pRS415. Positive transformants were isolated by blue color following growth in the presence of MMS and X-gal.

XXVII. cyd

I obtained a strain of *E. coli* containing a cyd-lacZ fusion integrated into the bacterial chromosome.

The nucleotide sequence of the cyd promoter was reported by G. N. Green et al., *J. Biol. Chem.*, 263, pp. 13138–143 (1988), the disclosure of which is herein incorporated by reference. Thus, a cyd-lacZ fusion can be constructed using the PCR technique described in Example 2, part II and the following primers: 5'-CGCCGAATTCGCG-GCGTAATATATACGTCCCATC-3' [SEQ ID NO:49]; and 5'-CGCGGGATCCCATGACTCCTTGCT-CATCGCATGAAG ACTCCG-3' [SEQ ID NO:50].

Transformants are screened for inducibility of β-galactosidase expression by incubation of the strain under anaerobic conditions.

XXVIII. zwf

I obtained a strain of *E. coli* containing a zwf-lacZ fusion integrated into the bacterial chromosome.

A zwf-lacZ fusion can be constructed using the PCR technique described in Example 2, part II and the following primers: 5'-CGCCGAATTCTGCCGCAGTTTGCGC GCTTTTCCCG-3' [SEQ ID NO:51]; and 5-GCGCGGATC-CGT CATTCTCCTTAAGTTAACTAACCCGG-3' [SEQ ID NO:52].

Transformants are screened for inducibility of β-galactosidase expression by incubation of strains in the presence of superoxide-producing compounds, such as paraquat, or in the presence of nitric oxide.

XXIX. groE

I obtained a strain of *E. coli* containing a groE-lacZ fusion integrated into the bacterial chromosome.

A groE-lacZ fusion can be constructed by first synthesizing the following two oligonucleotides which represented portions of the top and bottom strand of the groE promoter: 5'-CGCCGAATTCATCAGAATTTTTTTTCTT TTTC-CCCCTTGAAGGGGCGAAGCCTCATC-CCCATTTCTCTGGTCACCAGCC GGG-3' [SEQ ID NO:53]; and 5'-GCGCGGATCCCGGAGCTTACG TGGTTTCCCGGCTGGTGACCA-GAGAAATGGGGATGAGGCTTCGCCCCTTCA AGG-3' [SEQ ID NO:54].

The two oligonucleotides are annealed to one another and then incubated with Klenow fragment to complete synthesis of the double stranded promoter. The double stranded promoter is then digested with EcoRI and BamHI. The digested promoter is then cloned into EcoRI/BamHI digested pRS415. Positive transformants are grown in the presence of X-Gal and identified by a blue color following an increase in growth temperature of the cultures from 37° C. to 42° C. for 30 minutes.

XXX. aniG

I obtained the *E. coli* stain JF1295 (aniG1072::Mu dJ) from Dr. John Foster and Dr. Kevin Karem of the University of South Alabama College of Medicine. This strain contains a single copy of an anig-lacZ fusion in the bacterial chromosome. The construction of this strain is described in Z. Aliabadi et al., *J. Bacteriol.*, 170, pp. 842–51 (1988), the disclosure of which is herein incorporated by reference.

EXAMPLE 11

Method for Integrating Single Copy of Promoter-lacZ Fusion into Bacterial Chromosome In order to compare induction of the various promoters to one another it is necessary to standardize the copy number of each promoter fusion construct. This was achieved by using a recombinant lambda phage to integrate a single copy of the fusion into the bacterial chromosome.

*E. coli* strain SF1 carrying a stress promoter-lacZ fusion on a plasmid was grown in 5 ml of lambda broth (1% (w/v) tryprone, 0.1% (w/v) yeast extract, 0.2% (w/v) maltose and 0.25% (w/v) NaCl) at 37° C. until the cells reached a concentration of $5 \times 10^8$/ml. The cells were then centrifuged and the cell pellet was resuspended in 5 ml of 10 mM $MgSO_4$ and incubated at 37° C. for 1 hour with shaking.

I then added 100 µl of a dilution series of λRS88 [R. W. Simons et al., *Gene*, 53, pp. 85–96 (1987)] in SM buffer to 200 µl cells. The mixtures were incubated at 37° C. for 15–20 minutes with shaking. The entire 300 µl was then added to 3 ml of top agar [1% (w/v) tryptone, 0.1% (w/v) yeast extract, 0.2% (w/v) maltose, 0.25% (w/v) NaCl and 0.65% (w/v) agar] held at 45° C. and the mixture poured onto lambda agar plates [1% (w/v) tryptone, 1% (w/v) agar and 0.25% (w/v) NaCl]. The plates were incubated at 37° C. until visible plaques formed. The plate containing almost confluent plaques was used for the next step.

I next added 5 ml of SM buffer to the plate and carefully scraped off that solution together with the top agar into a glass tube. To this I added 1 ml chloroform and vortexed for 10 seconds. I then centrifuged the mixture, removed the upper phase of the supernatant, added 0.5 ml chloroform to the removed supernatant and stored at 4° C. The final phage lysate contained between $10^6$ and $10^{10}$ phage/ml. The frequency of recombinant phage containing the stress promoter fusion is about 1 in $10^4$ phage.

I next performed steps to integrate a single copy of the stress promoter fusion into the bacterial chromosome. I grew SF1 cells in 5 ml lambda broth at 37° C. to a concentration of $5 \times 10^8$ cells/ml. I then centrifuged the cells and resuspended them in 5 ml of 10 mM $MgSO_4$ and incubated at 37° C. for 1 hour with shaking. I then added 100 µl of a dilution series of the λRS88 stock in SM buffer to 200 µl cells. The mixtures were incubated at 37° C. for 15–20 minutes with shaking. The entire 300 µl was then added to 3 ml of top agar held at 45° C. and containing 400 µg/ml of X-Gal. The mixture was then poured onto lambda agar plates and the plates were incubated at 37° C. until visible plaques form. Blue plaques were picked by punching the agar with the back end of a sterile pipette and placing the agar plug into 200 μl of SM buffer and 50 μl of chloroform. The mixture was then vortexed until the agar clump was broken up. I then centrifuged the tube, removed the supernatant to a tube containing 50 μl of chloroform and stored it at 4° C. The picked plaques were repurified once and then a stock made from a plate containing almost confluent plaques.

In order to create a bacterial strain containing astress promoter fusion integrated into the bacterial chromosome, the above plaque stock was used to infect SF1 cells, as described above. Bacterial colonies present in the center of blue plaques were picked with a sterile pasteur pipette and placed in 0.5 ml LB. After incubation at 37° C. for 4–5 hours, the culture was streaked out onto LB/X-Gal plates and incubated at 37° C. overnight. Isolated blue colonies were picked and then checked for the presence of the particular stress promoter by incubation in the presence of a known inducer. Bacterial lysates were then analyzed for β-galactosidase activity. Colonies which demonstrated inducible β-galactosidase activity contained a single copy of the desired stress promoter fusion.

EXAMPLE 12

Additional Assays of Known Toxins Using Preferred Kit

I used the most preferred set of promoter fusions and the β-galactosidase assay, both described in Example 11, to generate an induction profile for MMS, HgCl, 4-NQO and paraquat.

Figure 9:
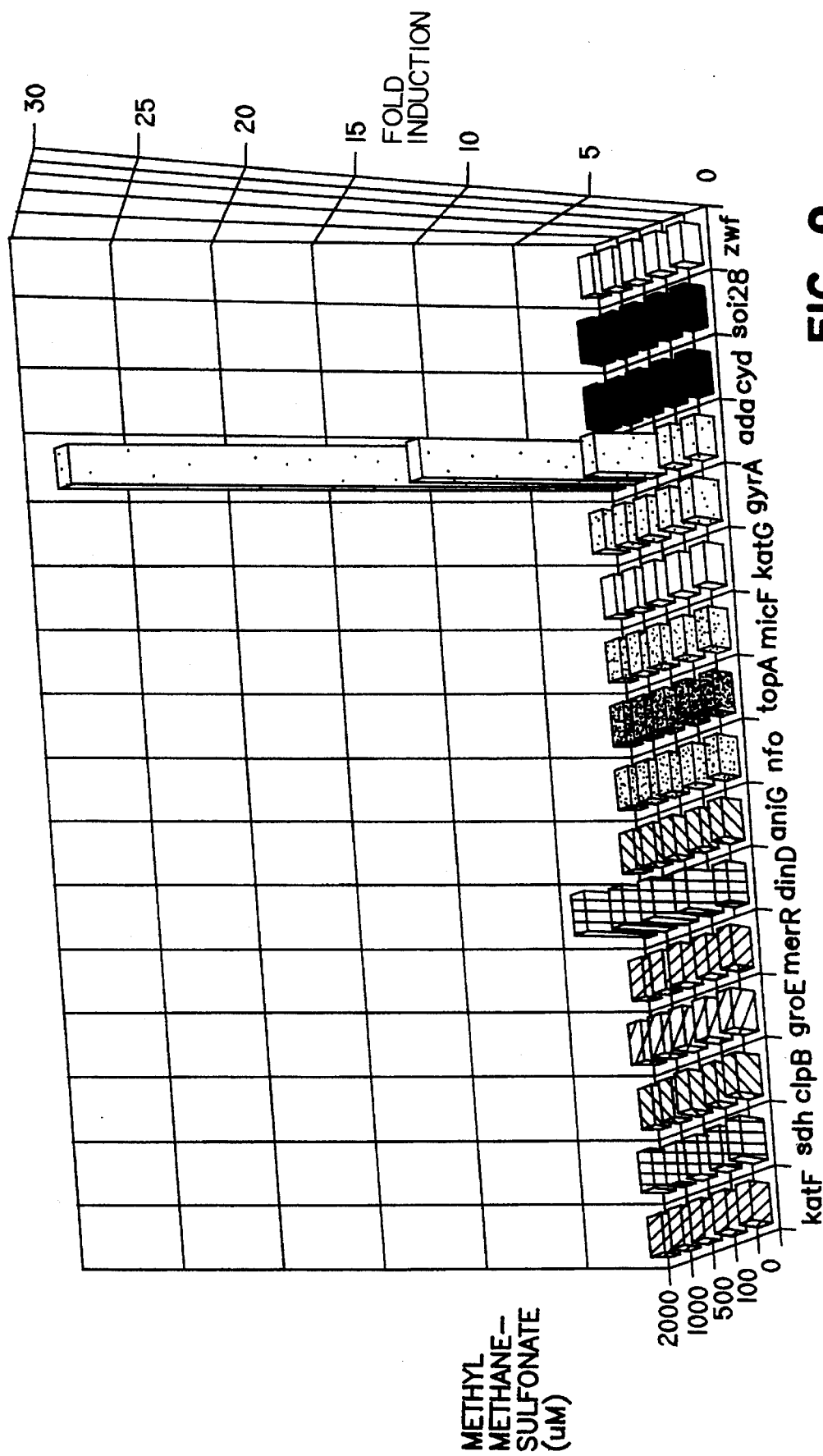
FIG. 9 depicts the effect of various concentrations of methyl methanesulfonate on the induction of each of the sixteen stress promoters in the most preferred diagnostic kit of this invention as measured by fold increase in β-galactosidase activity.

FIG. 9 demonstrates that MMS specifically induces the ada promoter and, to a much lesser degree, the dinD promoter at concentration of 470 μM to 1880 μM. This confirms the known mechanism of action of MMS which causes DNA damage primarily by alkylating DNA (ada induction). The minor induction of dinD may be the result of fortuitous DNA strand breaks.

Figure 10:
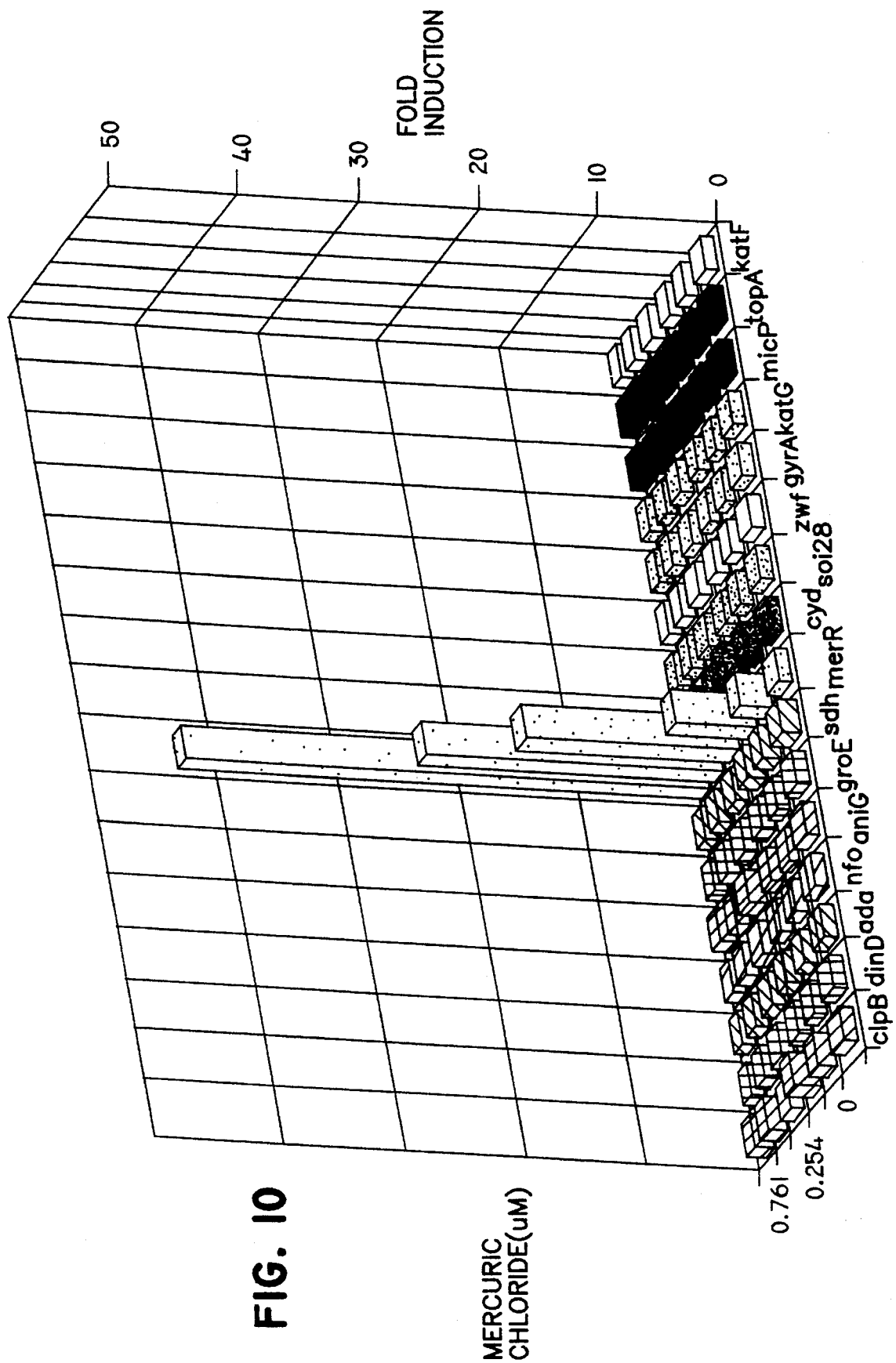
FIG. 10 depicts the effect of various concentrations of mercuric chloride on the induction of each of the sixteen stress promoters in the most preferred diagnostic kit of this invention as measured by fold increase in β-galactosidase activity.

FIG. 10 demonstrates that mercuric chloride specifically induces the merR promoter, which is known to respond to inorganic mercury compounds.

Figure 11:
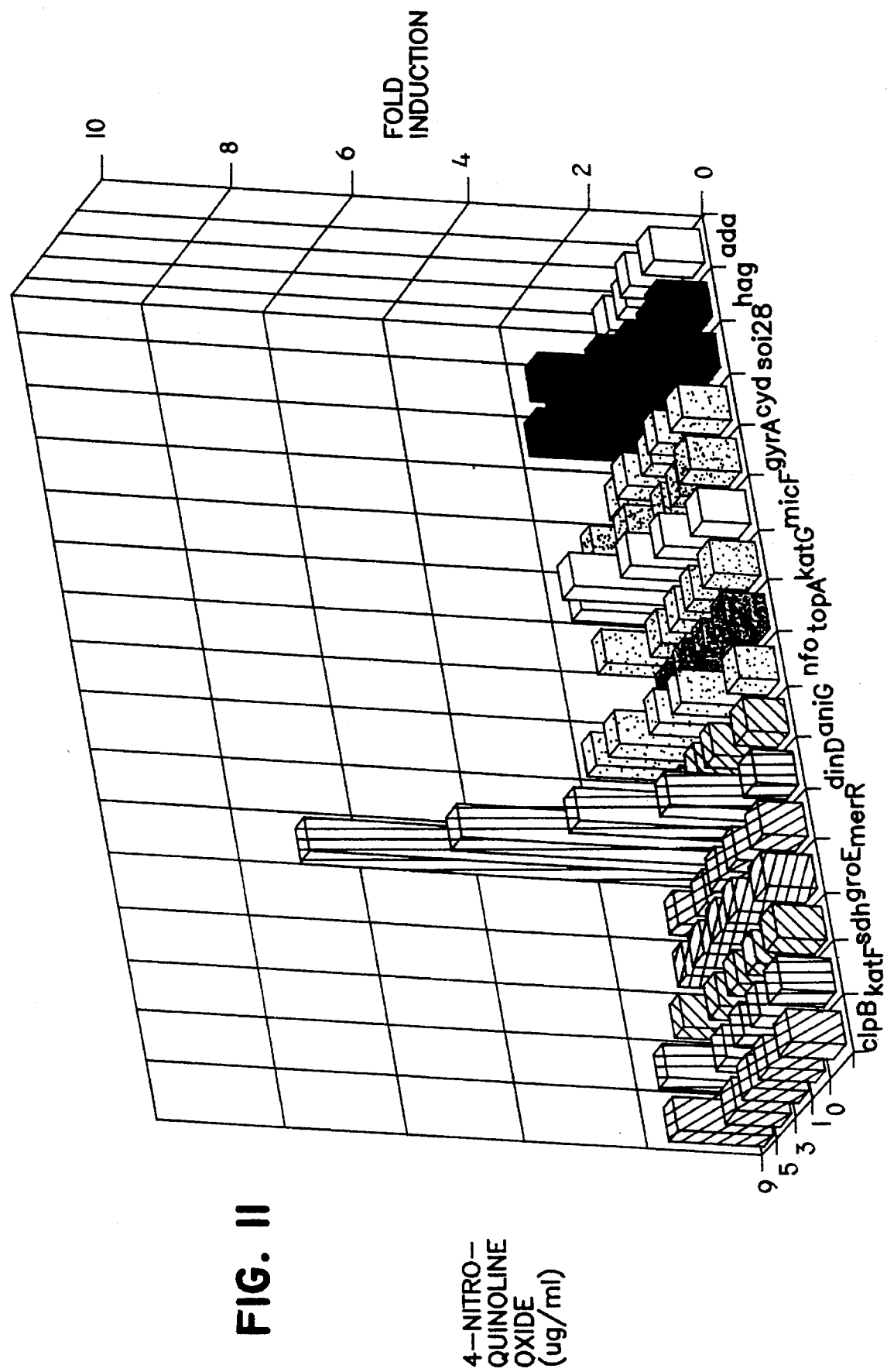
FIG. 11 depicts the effect of various concentrations of nitroquinoline oxide on the induction of each of the sixteen stress promoters in the most 3 preferred diagnostic kit of this invention as measured by fold increase in β-galactosidase activity.

FIG. 11 demonstrates that 4-NQO causes induction of the dinD promoter and, to a lesser extent, the soi28, nfo and micF promoters. This is consistent with the mode of action of 4-NQO which causes DNA damage via oxidative strand breaks, as well as disrupting the redox balance of the cell.

Figure 12:
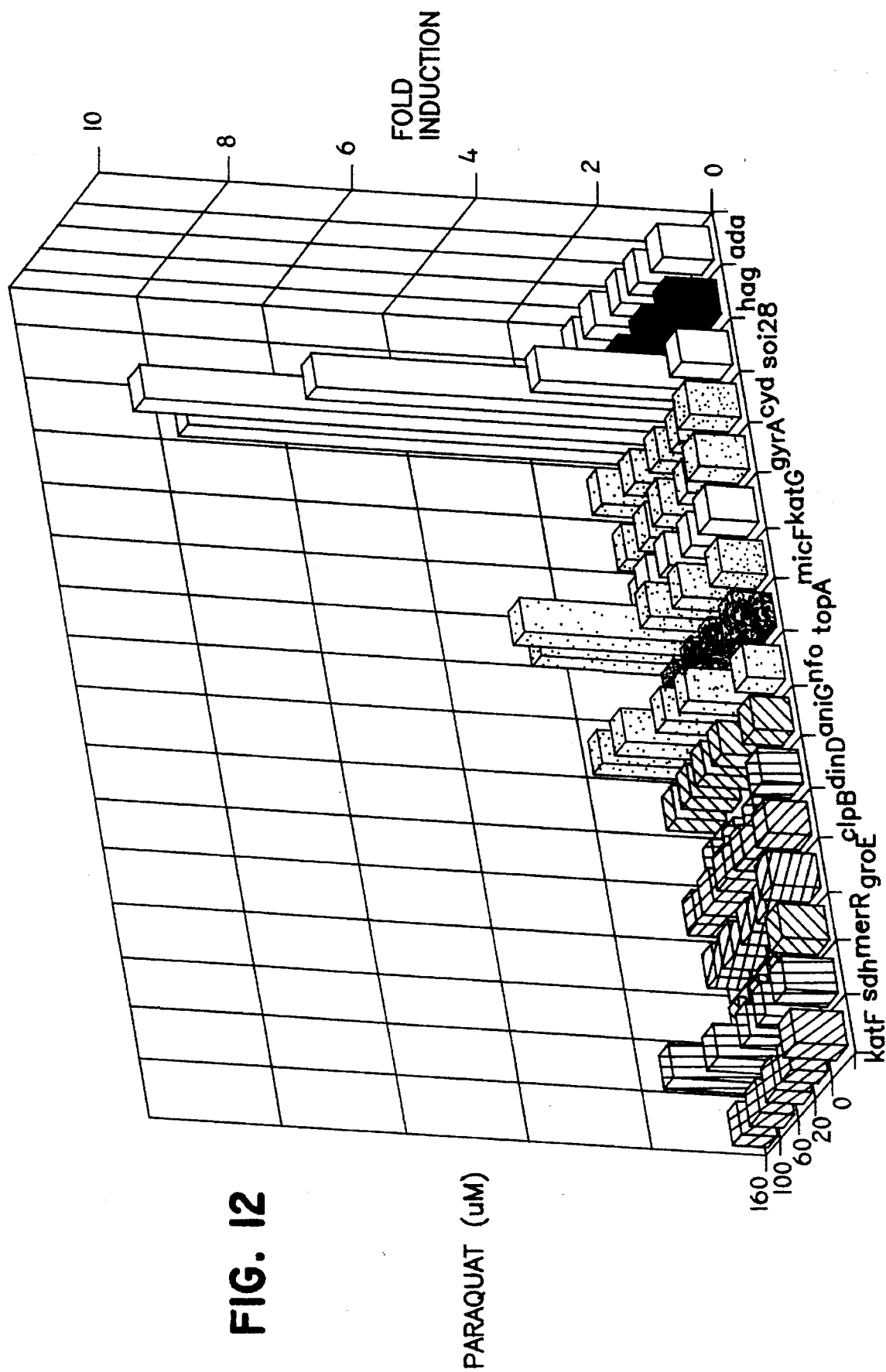
FIG. 12 depicts the effect of various concentrations of paraquat on the induction of each of the sixteen stress promoters in the most preferred diagnostic kit of this invention as measured by -fold increase in β-galactosidase activity.

FIG. 12 demonstrates the specific induction of the soi28 and micF promoters and, to a lesser extent, the nfo promoter by paraquat. Paraquat is known to cause superoxide radical formation which, in turn, induces redox stress promoters soi28 and micF. The nfo promoter is induced by oxidative DNA damage, which may be caused by high superoxide radical concentration within the cell. The apparent inhibition of the merR and dinD promoters cannot yet be explained.

In addition to the above studies, a large number of other chemicals were screened against the preferred promoter set, which consists of bacteria harboring single copies of the following bacterial stress promoters fused to β-galactosidase: soi28, dinD, hag, ada, gyr, katG, nfo, clpB, merR, top, cyd, micF, zwf, groE, katF and aniG. The results of these assays are presented below in Table 4.

TABLE 4

Effect of Various Compounds on the Stress Promoter Controlled Expression of β-Galactosidase

| Agent | High Conc. | Induced Promoter | Fold Induction | Concentration |
|---|---|---|---|---|
| Paraquat | 8 mg/ml | micF | 6.6 | 8 mg/ml |
| Paraquat | | zwf | 3 | 8 mg/ml |
| Paraquat | | soi28 | 12 | 8 mg/ml |
| Paraquat | | nfo | 3.4 | 8 mg/ml |
| Carbon Tetrachloride | 15 mg/ml | clpB | 2 | 15 mg/ml |
| Carbon Tetrachloride | | soi28 | 1.6 | 1 mg/ml |
| Trichloroethane | 15 mg/ml | clpB | 2 | 15 mg/ml |
| Trichloroethane | | soi28 | 1.4 | 2 mg/ml |
| Sodium Azide | 1 mg/ml | clpB | 2 | 40 μg/ml |
| Ethyl Methane-sulfonate | 1 mg/ml | | | |
| Methyl Methane-sulfonate | 5 mg/ml | ada | 48 | 200 μg/ml |
| Methyl Methane-sulfonate | | dinD | 5 | 200 μg/ml |
| Chloroform | 1% in 2% EtOH | clpB | 4.5 | 0.5% in 1% EtOH |
| Chloroform | | soi28 | 2 | 0.5% in 1% EtOH |
| Methanol | 15% (v/v) | | | |
| Ethanol | 10% (v/v) | soi28 | 1.7 | 6% (v/v) |
| Ethanol | | micF | 2.5 | 6% (v/v) |
| Phenol | 0.4% (v/v) | groE | 2.2 | 0.08% (v/v) |
| Phenol | | clpB | 1.5 | 0.08% (v/v) |
| 1-propanol | 20% (v/v) | groE | 1.5 | 4% (v/v) |
| 1-propanol | | clpB | 5.6 | 4% (v/v) |
| 1-propanol | | micF | 4 | 4% (v/v) |
| Methapyrilene HCl | 10 mg/ml | micF | 1.5 | 2 mg/ml |
| Methapyrilene HCl | | topA | 1.5 | 2 mg/ml |
| Methapyrilene HCl | | zwf | 2.7 | 2 mg/ml |
| Methapyrilene HCl | | groE | 1.7 | 2 mg/ml |
| Methapyrilene HCl | | clpB | 3 | 0.4 mg/ml |
| Methapyrilene HCl | | aniG | 2.3 | 0.4 mg/ml |
| N,N Dimethyl formamide | 10% | micF | 3.3 | 2% |
| N,N Dimethyl formamide | | zwf | 1.5 | 0.80% |

TABLE 4-continued

| Effect of Various Compounds on the Stress Promoter Controlled Expression of β-Galactosidase | | | | |
|---|---|---|---|---|
| Agent | High Conc. | Induced Promoter | Fold Induction | Concentration |
| N,N Dimethyl formamide | | clpB | 2.5 | 4% |
| Mercury orange | | gyrA | 2-3 | 40 ng/ml |
| Nalidixic acid | 5 mg/ml | gyrA | 2.5 | 0.32 µg/ml |
| Nalidixic acid | | katG | 3.2 | 0.32 µg/ml |
| Nalidixic acid | | micF | 3.4 | 200 µg/ml |
| Nalidixic acid | | dinD | 5.4 | 8 µg/ml |
| p-chloroaniline | 1 mg/ml | micF | 2 | 0.5 mg/ml |
| p-chloroaniline | | clpB | 3 | 1 mg/ml |
| Dinitrofluoro benzene | 5 mg/ml | micF | 3.2 | 0.32 mg/ml |
| Dinitrofluoro benzene | | clpB | 2 | 0.32 mg/ml |
| Lead nitrate | 2 mg/ml | | | |
| Cadmium chloride | 10 µg/ml | | | |
| Cadmium sulfate | 250 µg/ml | | | |
| Zinc chloride | 800 µg/ml | | | |
| Mercuric chloride | 7 µg/ml | merR | 27 | 2 ng/ml |
| Mitomycin C | 40 µg/ml | clpB | 3.2 | 10 µg/ml |
| Mitomycin C | | katF | 3 | 25 µg/ml |
| Mitomycin C | | dinD | 9 | 25 µg/ml |
| Sodium arsenate | 400 µg/ml | | | |
| Potassium arsenate | 300 µg/ml | | | |
| Lead acetate | 5 mg/ml | | | |
| Hydrogen peroxide | 30% | katG | 2 | 0.003% |
| Hydrogen peroxide | | dinD | 3 | 0.003% |
| Puromycin | 5 mg/ml | clpB | 1.5 | 20 µg/ml |
| Nitoquinoline oxide | 3.5 mg/ml | micF | 2.4 | 30 µg/ml |
| Nitoquinoline oxide | | soi28 | 2.6 | 2.6 µg/ml |
| Nitoquinoline oxide | | dinD | 7.5 | 10 µg/ml |
| Dithiothreitol | 5 mg/ml | gyrA | 2 | 0.5 mg/ml |
| Tert-butyl hydroquinone | 10 mM in DMSO | micF | 2.6 | 2 mM |
| Tert-butyl hydroquinone | | clpB | 2.8 | 2 mM |
| Formaldehyde | 40 µg/ml | | | |
| DMSO | 25% (v/v) | clpB | 2 | 25% (v/v) |
| DMSO | | dinD | 2.2 | 25% (v/v) |
| DMSO | | topA | 1.7 | 25% (v/v) |
| DMSO | | nfo | 1.6 | 25% (v/v) |

In the preceding table, "Agent" is the compound added to the bacterial cultures harboring the various stress promoter fusions; "High Conc." is the highest concentration of agent tested against those cultures; "Induced Promoter" is the stress promoter that was induced by a particular agent; "Fold Induction" is the level of stress-promoter controlled β-galactosidase expression in the presence of agent (at the concentration indicated in the "Concentration" column) compared to β-galactosidase expression in the absence of agent.

While I have hereinbefore presented a number of embodiments of this invention, it is apparent that my basic construction can be altered to provide other embodiments which utilize the diagnostic kits, processes and products of this invention. Therefore, it will be appreciated that the scope of this invention is to be defined by the claims appended hereto rather than the specific embodiments which have been presented hereinbefore by way of example.

I claim:

1. A diagnostic kit for determining the toxicity of a compound or identifying an antitoxin to a toxic compound, said kit comprising:
 a plurality of bacterial hosts, each of said hosts harboring a promoter which responds to stress, said promoter being operatively linked to a gene heterologous to said promoter and encoding an assayable product, wherein said plurality of hosts, in toto, comprise at least one promoter which responds to each of: redox stress, DNA stress, protein stress, energy stress and pH stress.

2. The diagnostic kit according to claim 1, wherein said promoter which responds to redox stress is sodA, soi28, katG, ahp, rdc, gsh, zwf or micF.

3. The diagnostic kit according to claim 1, wherein said promoter which responds to DNA stress is dinD, ada-alkA, ada, leu-500, gyr, top, mutT or nfo.

4. The diagnostic kit according to claim 1, wherein said promoter which responds to protein stress is rpoD, lon, clpB, merR, fepB-entC, groE or meto.

5. The diagnostic kit according to claim 1, wherein said promoter which responds to energy stress is sdh, cyo, cyd or unc.

6. The diagnostic kit according to claim 1, wherein said promoter which responds to pH stress is hag, micF, aniG or katF.

7. The diagnostic kit according to claim 1, wherein said plurality of bacterial hosts, in toto, comprises the promoters: soi28, dinD, hag, ada, gyr, katG, nfo, clpB, merR, top, cyd, micF, zwf, groE, katF and aniG.

8. The diagnostic kit according to claim 7, further comprising which is rdc, ahp, lon, unc, fepB-entC, leu-500, cyo, sdh, rpoD, ada-alkA, sodA, mutT, gsh or meto.

9. The diagnostic kit according to any one of claims 1 to 8, wherein said gene encoding an assayable product is lacZ.

10. A method for determining the toxicity of a compound comprising the steps of:
   (a) separately culturing each of a plurality of bacterial hosts, wherein each of said hosts harbors at least one promoter which responds to stress, said promoter being operatively linked to a gene heterologous to said promoter and encoding a detectable product, and wherein said plurality of hosts comprise, in toto, promoters which respond to each of: redox stress, DNA stress, protein stress, energy stress and pH stress;
   (b) incubating each of said cultures with said compound;
   (c) quantifying said detectable product in each culture; and
   (d) creating a stress promoter induction profile for said compound.

11. The method according to claim 10, wherein said promoter which responds to redox stress is sodA, katG, ahp, soi28, rdc, gsh, micF or zwf.

12. The method according to claim 10, wherein said promoter which responds to DNA stress is dinD, ada-alkA, ada, leu-500, gyr, top, mutT or nfo.

13. The method according to claim 10, wherein said promoter which responds to protein stress is rpoD, lon, clpB, merR, fepB-entC, meto or groE.

14. The method according to claim 10, wherein said promoter which responds to energy stress is sdh, cyo, cyd or unc.

15. The method according to claim 10, wherein said promoter which responds to pH stress is hag, katF, micF or aniG.

16. The method according to claim 10, wherein said plurality of bacterial hosts, in toto, comprises the promoters: soi28, dinD, hag, ada, gyr, katG, nfo, clpB, merR, top, cyd, micF, zwf, groE, katF and aniG.

17. The method according to claim 16, wherein said plurality of bacterial hosts further comprises which is rdc, ahp, lon, unc, fepB-entC, leu-500, cyo, sdh, rpoD, ada-alkA, sodA, mutT, gsh or meto.

18. The method according to any one of claims 10 to 17, comprising the additional step of incubating said compound with an S9 liver extract, prior to step (b).

19. The method according to claim 18, wherein said gene encoding a detectable product is lacZ.

20. A method of identifying an antitoxin to a toxic compound comprising the steps of:
   (a) determining the type of stresses caused by said toxic compound by the process according to claim 18;
   (b) identifying a known toxic compound which, in the process according to claim 18, causes similar stresses to the stresses caused by said toxic compound; and
   (c) identifying an antitoxin to said known toxic compound.

21. The method according to any one of claims 10 to 17, wherein said gene encoding a detectable product is lacZ.

22. A method of identifying an antitoxin to a toxic compound comprising the steps of:
   (a) determining the type of stresses caused by said toxic compound by the process according to claim 19;
   (b) identifying a known toxic compound which, in the process according to claim 19, causes similar stresses to the stresses caused by said toxic compound; and
   (c) identifying an antitoxin to said known toxic compound.

23. A method of identifying an antitoxin to a toxic compound comprising the steps of:
   (a) determining the type of stresses caused by said toxic compound by the process according to any one of claims 10–17;
   (b) identifying a known toxic compound which, in the process according to any one of claims 10–17, causes similar stresses to the stresses caused by said toxic compound; and
   (c) identifying an antitoxin to said known toxic compound.

* * * * *